United States Patent [19]

Mainiero et al.

[11] Patent Number: 5,715,816

[45] Date of Patent: Feb. 10, 1998

[54] OXIMETER PROBES AND METHODS FOR THE INVASIVE USE THEREOF

[75] Inventors: Louis M. Mainiero, Delafield; Robert L. Young, Waukesha; Stephen H. Gorski, Eagle, all of Wis.

[73] Assignee: Sensor Devices, Inc., Waukesha, Wis.

[21] Appl. No.: 546,246

[22] Filed: Oct. 20, 1995

Related U.S. Application Data

[63] Continuation-in-part of Ser. No. 412,287, Mar. 28, 1995, which is a continuation-in-part of Ser. No. 163,052, Dec. 6, 1993, Pat. No. 5,417,207.

[51] Int. Cl.$^6$ .................................................. A61B 5/00
[52] U.S. Cl. ............................................................ 128/633
[58] Field of Search ........................................ 128/632, 633, 128/634, 637, 664, 665, 666, 667, 207.15, 204.23, 205.23, 200.26; 604/93, 264; 356/39, 40, 41

[56] References Cited

U.S. PATENT DOCUMENTS

| | | |
|---|---|---|
| Re. 31,377 | 9/1983 | Mylrea et al. . |
| 3,734,094 | 5/1973 | Calinog . |
| 3,951,136 | 4/1976 | Wall . |
| 4,090,518 | 5/1978 | Elam . |
| 4,176,660 | 12/1979 | Mylrea et al. . |
| 4,301,809 | 11/1981 | Pinchak et al. . |
| 4,349,031 | 9/1982 | Perlin . |
| 4,475,555 | 10/1984 | Linder . |
| 4,476,872 | 10/1984 | Perlin . |
| 4,484,583 | 11/1984 | Graham . |
| 4,574,807 | 3/1986 | Hewson et al. . |
| 4,619,268 | 10/1986 | Uphold et al. . |
| 4,640,298 | 2/1987 | Pless et al. . |
| 4,671,296 | 6/1987 | Aitken ................................ 128/671 |
| 4,672,971 | 6/1987 | Otten . |
| 4,763,663 | 8/1988 | Uphold et al. . |
| 4,848,352 | 7/1989 | Pohndorf et al. . |
| 4,930,521 | 6/1990 | Metzger et al. . |
| 4,960,133 | 10/1990 | Hewson . |
| 4,967,759 | 11/1990 | Teves . |
| 4,981,470 | 1/1991 | Bombeck . |
| 5,005,573 | 4/1991 | Buchanan . |
| 5,052,390 | 10/1991 | Hewson . |
| 5,154,387 | 10/1992 | Trailer . |
| 5,191,892 | 3/1993 | Blikken . |
| 5,193,544 | 3/1993 | Jaffe . |
| 5,247,932 | 9/1993 | Chung et al. ......................... 128/633 |
| 5,282,464 | 2/1994 | Brain ................................... 128/633 |
| 5,329,922 | 7/1994 | Atlee . |
| 5,357,954 | 10/1994 | Shigezawa et al. . |
| 5,411,024 | 5/1995 | Thomas et al. . |
| 5,417,207 | 5/1995 | Young et al. . |

FOREIGN PATENT DOCUMENTS

| | | |
|---|---|---|
| WO 91/15151 | 4/1991 | European Pat. Off. . |
| 0 484 547 A1 | 5/1991 | European Pat. Off. . |
| 0 575 737 A1 | 5/1993 | European Pat. Off. . |
| 29 42 178 A1 | 10/1979 | Germany . |

OTHER PUBLICATIONS

*Sexual Instrumentaion,* by John L. Semmlow and Jack Lubowsky, IEEE Transactions on Bomedical Engineering, vol. BME–30 (1983) Jun., No. 6, New York, USA.

H.R. Andersen and P. Pless, *Trans–Esophageal Pacing,* PACE, vol. 6, Jul.–Aug. 1983.

*Primary Examiner*—Jennifer Bahr
*Assistant Examiner*—Eric F. Winakur
*Attorney, Agent, or Firm*—Snell & Wilmer

[57] ABSTRACT

A probe useful for invasively monitoring the oxygen saturation level of blood in the tissue walls of an anatomical cavity generally comprises a chassis with an electrical connector extending from the proximal end of the chassis and terminating at a plug configured for connection to a pulse oximeter box. The probe further includes an optics assembly configured to generate and transmit electrical signals that are indicative of the dynamic oxygen saturation level of blood in the wall tissue. The probe further includes a deployment device attached to the chassis for biasing the optics assembly into the tissue wall of the anatomical canal and stabilizing the probe within the canal. Further, the oximetry sensing assembly may be configured as part of an esophageal stethoscope having other sensing devices, for example, a temperature sensor, a pacing assembly, and an acoustic monitor.

34 Claims, 12 Drawing Sheets

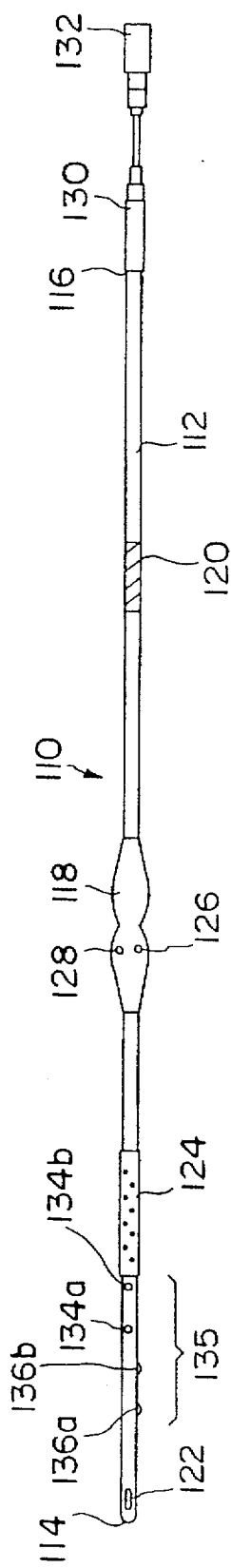
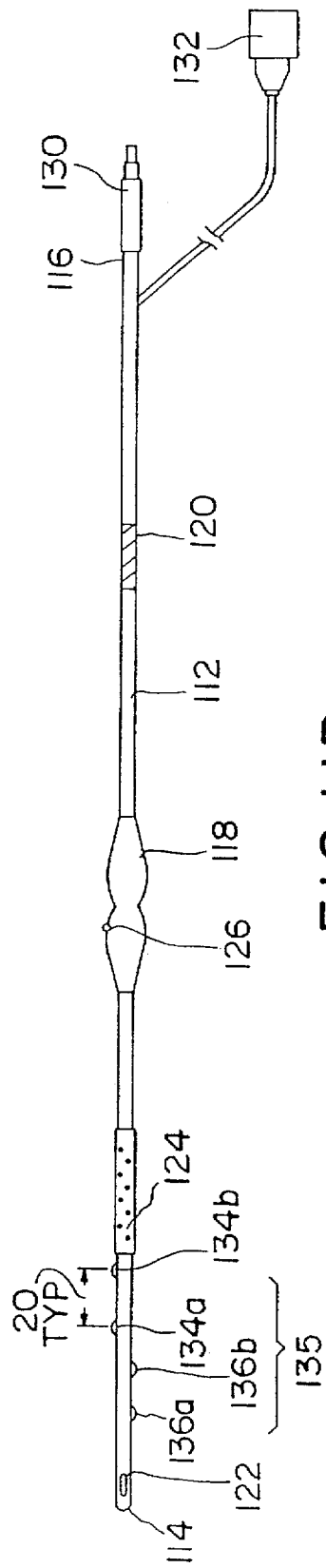
FIG. 11A
FIG. 11B

OXIMETER PROBES AND METHODS FOR THE INVASIVE USE THEREOF

CROSS-REFERENCE TO RELATED APPLICATIONS

This is a continuation-in-part of U.S. Ser. No. 08/412,287 filed Mar. 28, 1995, which in turn was a continuation-in-part of U.S. Ser. No. 08/163,052 filed Dec. 6, 1993, now U.S. Pat. No. 5,417,207 issued May 23, 1995; the subject matter of application Ser. No. 08/412,287 and application Ser. No. 08/163,052 are incorporated herein by reference.

TECHNICAL FIELD

The present invention relates, generally, to pulse oximetry, and more particularly to the invasive, in vivo use of oximeter probes in anatomical Canals of humans and animals.

BACKGROUND OF THE INVENTION

Pulse oximetry, involving the continuous, non-invasive monitoring of oxygen saturation level in blood perfused tissue, is becoming an increasingly important mechanism for determining patient condition both during and following medical procedures. Indeed, the use of pulse oximeters has expanded in recent years to the point where they are now considered essential in the context of many surgical, emergency room, intensive care, and neonatal applications. The use of pulse oximetry is also expanding into the areas of out-patient surgery centers, oral maxillofacial surgery, home care, and in the veterinary environment.

Pulse oximetry typically involves the use of an oximeter probe (sensor) in contact with the patient. The sensor provides an electrical output signal to an oximeter box, which houses electronic circuitry used to process the electrical signal and generate human-readable indicia of various physiological parameters, including the patient's blood oxygen saturation level and pulse rate. Pulse oximetry systems are currently available from a number of manufacturers, including model No. N-200 manufactured by Nellcor of Chula Vista, Calif.

Non-invasive pulse oximeter probes have traditionally employed transmittance technology, whereby light is passed through a portion of the patient's blood perfused tissue and analyzed to determine the blood saturation level of the tissue. More particularly, traditional oximeter probes comprise an LED assembly and a photodetector assembly spaced apart from each other and mounted to a flexible substrate. This substrate is configured to be attached to a convex portion of the patient's anatomy, for example a finger, toe, ear, and in the case of neonatal applications, to the ball of the foot. The oximeter probe may be conveniently attached to the patient by adhesives, a spring clip, Velcro, and the like. See, for example, Young, et al., U.S. Pat. No. 5,217,012 issued Jun. 8, 1993.

When properly attached to a patient, a transmittance oximeter probe is configured such that light emitted by the LED assembly passes through the patient's blood perfused tissue and is received by the photosensor assembly. The absorption characteristics of the transilluminated tissue are related to the oxygen saturation level of hemoglobin flowing through the tissue. Changes in the hemoglobin absorption characteristics influence the amount of light received by the photosensor, thus permitting the direct, non-invasive monitoring of arterial oxygen content. The photosensor assembly produces an output signal indicative of blood oxygen saturation level.

More recently, reflectance technology has been employed in the context of oximeter probes. Reflectance technology involves the use of an emitter assembly and a detector assembly mounted on a substrate and attached to the patient in an essentially co-planar fashion, for example on a patient's forehead or chest. When so mounted, light emitted by the emitter assembly passes through the patient's epidermis and is variously scattered and absorbed by the capillary and arterial beds, sweat glands, sebaceous glands, hair follicles, and the like beneath the patient's skin. During steady state operation of a reflectance probe, changes in the blood oxygen level of the blood perfused tissue proximate the sensor influence the amount of light received by the photosensor assembly in a manner analogous to transmission probes.

The theory of pulse oximetry, whether employed in the context of reflection or transmission sensing devices, is that the light received by the photosensor assembly and, hence, the blood oxygen level of the associated tissue, is a function of, inter alia, the relatively constant absorption characteristics of tissue, venus blood, and the like, as well as the variable absorption characteristics resulting from pulsations in arterial blood flow. Stated another way, the signal emitted by the photosensor assembly includes a DC component which is substantially independent of changes in blood oxygen saturation level, as well as a pulsatile AC component reflective of changes in blood oxygen saturation level.

In order to properly interpret changes in the oxygen saturation level of blood perfused tissue, a reasonably stable arterial pulsation is desired; indeed, an optical differencing measurement is typically made in accordance with this pulsation to determine the patient's pulse rate and oxygen saturation level. Moreover, a certain minimum threshold level of perfusion is generally needed in order to accurately detect changes in blood oxygen saturation level.

While suitable perfusion often exists at extremity sites (e.g., fingers, toes), a number of circumstances inhibit proper perfusion. For example, even in healthy pediatric and neonatal patients, lower mean arterial pressure and smaller arterial pathways inherently restrict the level of perfusion available for interrogation, particularly at the extremities. Moreover, in adults, conditions of critical illness, lowered body temperature, shock, trauma, burn, and other circumstances limit perfusion level as well as the ability to properly interface a sensor to a particular anatomical site. Accordingly, in many risk groups, conventional pulse oximeters are poorly adapted to situations wherein they are most needed. Moreover, many environmental factors, including the effects of changes in ambient light, humidity, and patient movement limit the practical utility of conventional oximeter sensors.

Thus, there exists a long felt need for an alternate site and monitoring configuration that positively addresses the limitations of presently known sensors.

SUMMARY OF THE INVENTION

An invasive electro-optical sensor probe according to the present invention addresses many of the shortcomings of the prior art.

In accordance with one aspect of the present invention, an oximeter sensing system is suitably disposed on an elongated, flexible chassis. The chassis is suitably configured for insertion into an anatomical canal, for example in the esophagus, rectum, or vaginal cavity of a human patient. Inasmuch as the hemoglobin oxygen transport mechanism is substantially identical for all mammals as well as many other animals, the reflectance and transmittance probes in accordance with the present invention, may also be suitably employed in the context of many veterinary applications. This is particularly advantageous inasmuch as many animals are poorly suited for conventional transmittance and reflectance probes due to the presence of hair, fur, and other complications associated with skin thickness, pigmentation, and the like.

In accordance with a further aspect of the present invention, the oximeter sensing assembly is suitably configured for use in the context of an anatomical cavity, for example the esophagus or rectal canal, wherein the sensing assembly is stabilized in a generally blood perfuse vascular region of the anatomical cavity through use of a uniquely configured deployment device. Such a configuration advantageously ensures that a desired optical path through a vascular bed of the tissue is obtained.

In accordance with still a further aspect of the present invention, the oximeter sensing assembly comprises emitter and detector assemblies which are suitably configured and placed to isolate vascular signals within the blood perfuse region of the anatomical canal in which the probe is used.

In accordance with a further aspect of the present invention, the oximeter sensing assembly secured to a deployment device is used in conjunction with existing invasive medical apparatus, for example in the context of an endotracheal tube or a core body temperature probe; in such context, the deployment device together with the emitter and detector assemblies may be suitably "piggybacked" onto or integrated with the endotracheal, temperature probe, or other such assemblies.

In accordance with a further aspect of the present invention, the probe is suitably configured for insertion into the esophagus, and as such, includes a deployment device suitably configured as a crico-pharyngeal ("CP") "lock" which substantially secures the probe and the oximetry sensors within the esophagus, greatly minimizing probe movement and enhancing oximetry measurement accuracy. The CP lock also serves as an esophageal diropter which serves to prevent fluids and other matter from passing-up and being aspirated by the patient.

In accordance with a further aspect of the present invention, the probe is suitably configured for insertion into a rectal canal, and as such, includes a deployment device which comprises a plug which substantially secures the probe and the oximetry sensors within the rectal canal.

BRIEF DESCRIPTION OF THE DRAWING FIGURES

The present invention will be hereinafter described in conjunction with the appended drawing figures, wherein like designations denote like elements, and:

FIG. 11A shows a top view of a further embodiment of a probe in accordance with the present invention;

FIG. 11B is a side view of the probe of FIG. 11A;

DETAILED DESCRIPTION OF PREFERRED EXEMPLARY EMBODIMENTS

Figure 1:
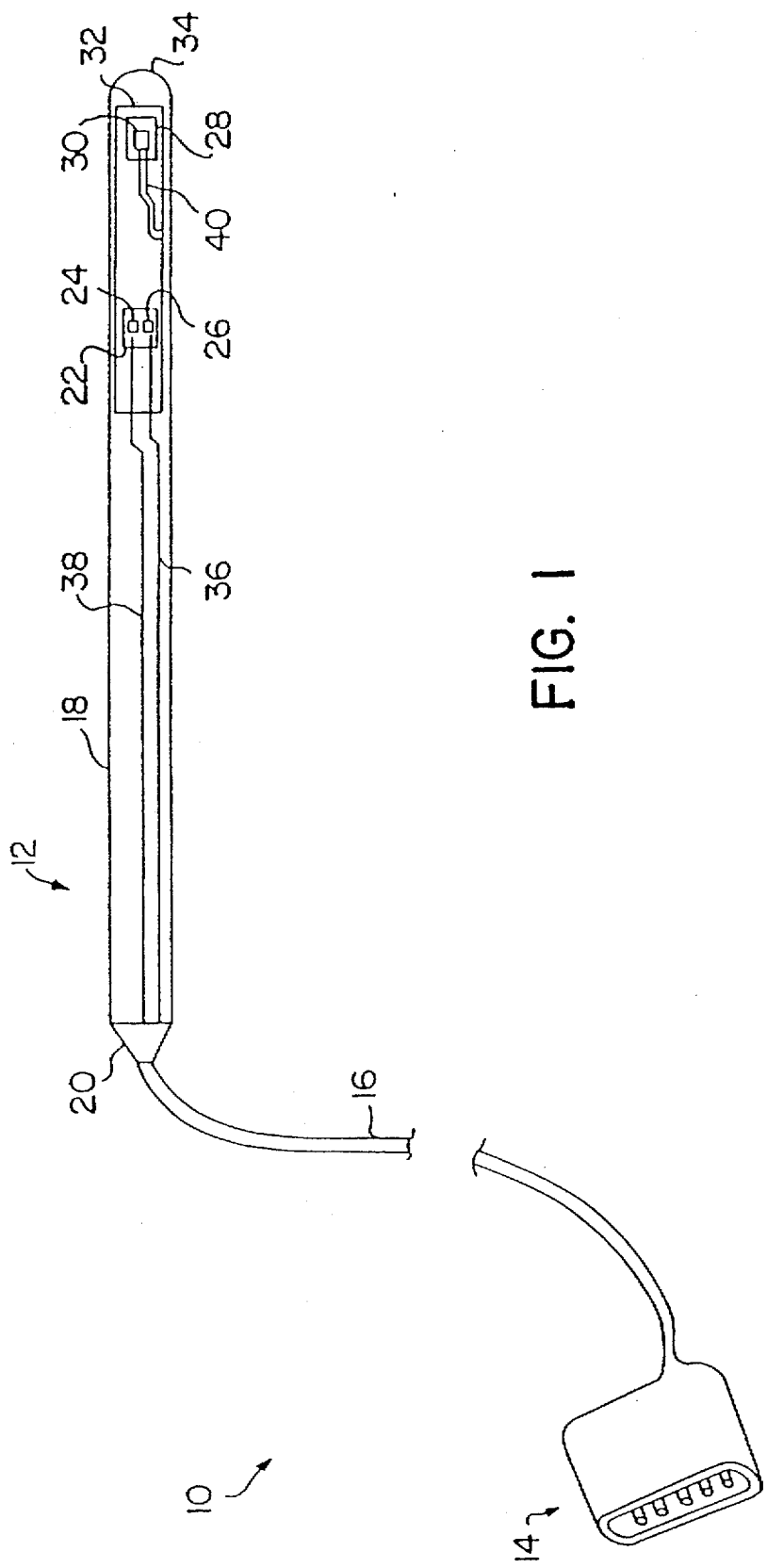
FIG. 1 is a top view of a reflectance probe in accordance with the present invention.

Referring now to FIG. 1, an exemplary probe assembly 10 suitably comprises a chassis 12, a plug 14, and an electrical cable 16 connecting chassis 12 with plug 14. Plug 14 is illustratively configured for attachment to an oximeter box or other output assembly configured to display indicia of, inter alia, blood oxygen saturation level, pulse rate, and the like.

In accordance with a preferred embodiment of the present invention, chassis 12 is suitably configured to be removably inserted into an anatomical canal, for example, the esophagus or rectum of a human or animal. Accordingly, cable 16 may be advantageously attached to chassis 12 via a junction 20 which securely grasps cable 16. Moreover, in accordance with a particularly preferred exemplary embodiment, junction 20 and chassis 12 are advantageously of integral, unitary construction to ensure that the device may be completely removed, intact, from an anatomical canal.

In accordance with a further aspect of the present invention, chassis 12 is suitably made from any desired biocompatible material, for example, polyurethane, polyethylene, PVC, PTFE, and/or the like. In accordance with a further aspect of the present invention, chassis 12 may be rigid, semi-rigid, flexible, or any desired degree of resiliency, depending on the particular application. For example, if the device is configured for use within the rectum of a large animal, e.g., a horse, a higher degree of rigidity may be appropriate. On the other hand, if the device is to be used in the esophagus or trachea in a child or an infant, a high degree of flexibility may be appropriate. Moreover, chassis 12 may comprise any suitable shape in cross-section, depending on, inter alia, the geometry of the anatomical canal within which the device is to be inserted, the geometry and topology of the optics associated with the device, and the use of the device in conjunction with other medical apparatus, as discussed in greater detail below. In this regard, chassis 12 may be suitably circular, elliptical, semispherical, arcuate, or substantially flat in cross-section, as desired.

With continued reference to FIG. 1, sensor 10 further comprises an emitter assembly 22 and a detector assembly 28 mounted on the surface of or within chassis 12. More particularly, emitter assembly 22 suitably comprises one or more light-emitting diodes (LEDs); in the illustrated embodiment, emitter assembly 22 comprises a first LED 24 having a wire 38 connected thereto, and a second LED 26 having a wire 36 connected thereto. Further, said LEDS are electrically connected in parallel such that electrical current flowing in one direction through wires 36 and 38 will cause the first LED 24 to operate, and electric current flowing in the opposite direction will cause first LED 24 to cease operation and cause second LED 26 to operate. Respective wires 36, 38 extend along the length of chassis 12, through junction 20, and into cable 16.

Detector assembly 28 suitably comprises a detector 30 configured to sense at least a portion of the output of emitter 22. In the illustrated embodiment, detector 30 comprises a photodetector, for example, a photodiode. A suitable pair of wires 40 interconnects detector 30 and plug 14 via cable 16.

With continued reference to FIG. 1, emitter assembly 22 and detector assembly 28 are suitably mounted to a spacer 32 to thereby maintain a constant spacing between the emitter and detector assemblies.

Emitter assembly 22 and detector assembly 28 are suitably mounted on the surface of or within chassis 12 in a manner which permits light emitted by emitter assembly 22 to pass through the blood perfused tissue interrogated by sensor 10 and to be received by detector assembly 28. If the emitter and detector assemblies are to be mounted within chassis 12, at least the distal portion of chassis 12 proximate the emitter and detector assemblies advantageously comprises a transmissive material to permit light to pass therethrough in the vicinity of emitter 22 and detector 28. Alternatively, emitter assembly 22 and detector assembly 28 may be mounted on the surface of or integral with the outer wall of chassis 12. In accordance with an alternate embodiment of the present invention, the emitter and detector may suitably be mounted within or otherwise integral with various other medical apparatus, for example, a temperature probe, an endotracheal tube, catheter, and the like.

Figure 2A:
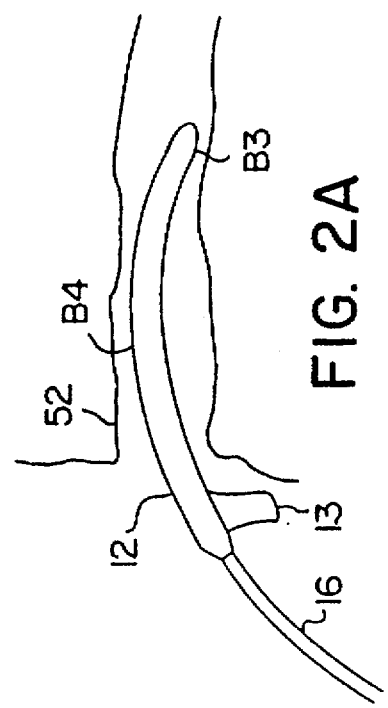
FIG. 2A shows an alternate configuration of the sensor of FIG. 2.
Figure 2:
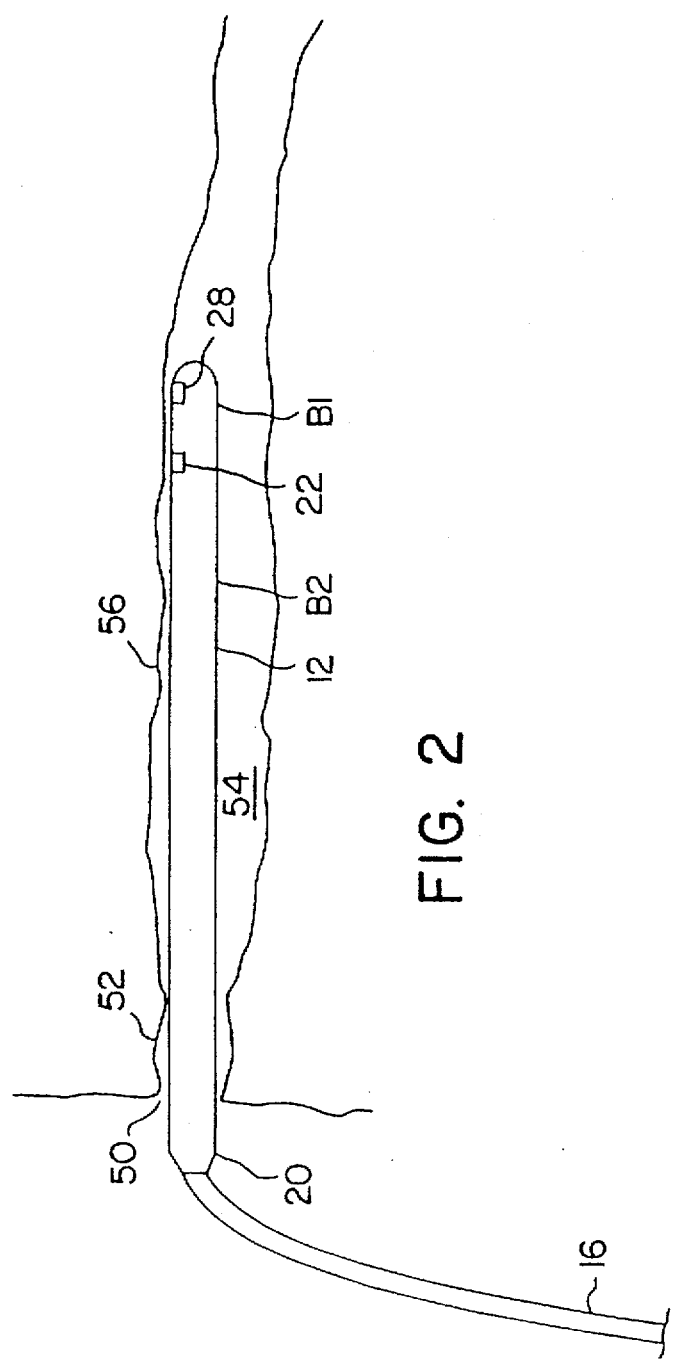
FIG. 2 shows an exemplary probe inserted into an anatomical canal.

Referring now to FIG. 2, chassis 12 is suitably configured for insertion into an anatomical canal 50, for example, the esophagus or a rectum of a human or animal. More particularly, canal 50 suitably comprises an opening 52, which may comprise a sphincter, a canal passageway 54, and a canal wall 56. In accordance with one aspect of the present invention, chassis 12 is desirably configured such that emitter assembly 22 and detector assembly 28 may be positioned proximate wall 56, suitably in intimate contact therewith.

In accordance with a further aspect of the invention, chassis 12 is suitably configured such that it may be inserted within canal 50 to any desired length, such that junction 20 remains outside the canal. In this regard, it may be desirable to equip chassis 12 with wings (not shown) or other structure in the vicinity of junction 20 to prevent the device from being inserted within the canal beyond junction 20.

Figure 3:
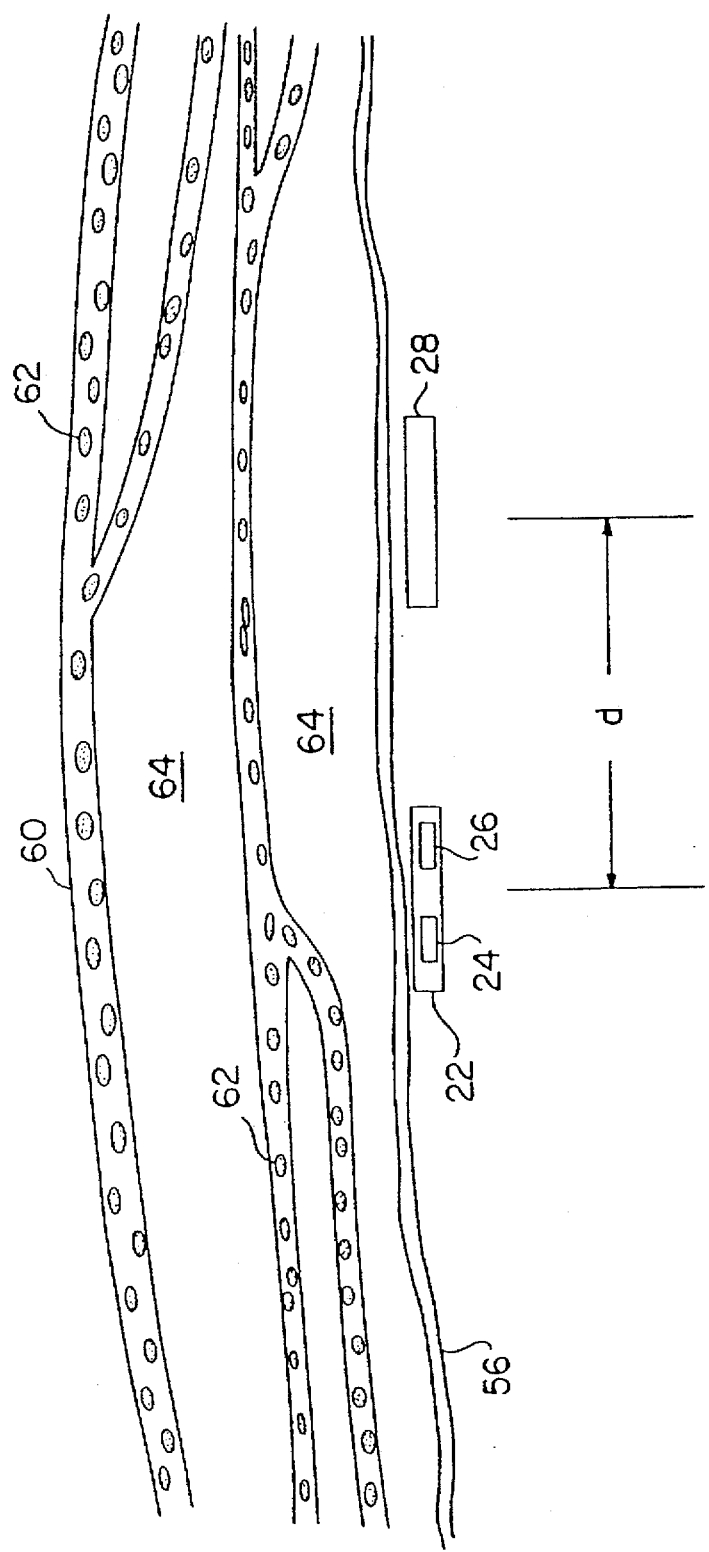
FIG. 3 is a schematic representation of an emitter and detector assembly disposed in situ, and showing the subdermal arterial hemoglobin transport mechanism for a typical patient.

Referring now to FIG. 3, in accordance with one aspect of the present invention, sensor 10 is inserted into canal 50 wherein canal wall 56 suitably comprises a mucus membrane, with dermal and subdermal tissue 64 laying beneath the surface of wall 56. An arterial bed comprising various arteries 60 suitably extends throughout the subdermal region proximate wall 56. The arterial blood carried by arteries 60 includes, among other things, blood cells (not shown) and particulate hemoglobin 62.

Pulse oximeters employ the principal of differential light absorption to determine the level of oxygen saturation of hemoglobin in arterial blood. In particular, the light absorption characteristics of oxyhemoglobin are very different from the light absorption characteristics of deoxyhemoglobin. Furthermore, the extinction coefficient for a hemoglobin solution is related to the absorption coefficient of the hemoglobin divided by the concentration. The absorption coefficient of a blood sample, which can be determined based on its oxygenation level and the extinction coefficients associated with the various components of the blood sample, is dependent upon both the wavelength of light used to interrogate the blood sample, as well as the oxygen saturation level of the blood sample.

With continued reference to FIG. 3 and in accordance with this aspect of the present invention, light emitted by emitter assembly 22, which is suitably proximate to or in intimate contact with wall 56, passes through tissue 64, arteries 60, and hemoglobin 62. In so doing, a portion of the light is absorbed by these constituents, and some of the light is scattered by these same constituents. The amount of scattered light which is received by detector assembly 28 is a function of, inter alia, the spacing D between emitter 22 and receptor 28, the size and configuration of emitter 22 and detector 28, and the oxygen saturation level of hemoglobin 62 with the arterial bed proximate the probe. By monitoring a characteristic of the output of detector Circuit 28 (e.g., voltage, typically current), the oxygen saturation level of the blood perfused tissue may be dynamically and continuously ascertained.

In accordance with a particularly preferred embodiment, two wavelengths of light, for example red and infra-red, are desirably emitted by first LED 24 and second LED 26, respectively. As stated above, the light absorption characteristics of oxygenated hemoglobin differ markedly from the absorption characteristics of deoxygenated hemoglobin; at the same time, the difference in absorption characteristics of oxygenated and deoxygenated hemoglobin is also a function of wavelength. In accordance with a preferred embodiment of the invention, the light emitted from emitter 22 is suitably chopped, such that emitter 24 is turned on for a predetermined period, then turned off for a predetermined period to allow the electronics to settle; thereafter, emitter 26 is energized for a predetermined period and thereafter turned off for a predetermined period, and the cycle is repeated. In this way, detector 28 ultimately receives a portion of light emitted at the first wavelength, and thereafter receives a portion of the light emitted at the second wavelength, in a repetitive fashion. As is known in the art, by monitoring two different wavelengths of light, the system can compensate for fluctuations in the level of light received by detector 28 which are unrelated to the level of oxygen saturation of the underlying hemoglobin. See, for example, *Pulse Oximeters*, 185–189 *Health Devices*, Vol. 18, No. 6, (June, 1989); Cui and Ostrander "In Vivo Reflectance On Blood And Tissue As A Function Of Light Wavelength", 630–639, *IEEE Transactions On Biomedical Engineering*, Vol. 37, No. 6 (June, 1990); and Decker, Dickensheets, Arnold, Cheung and Strohl, "A Comparison Of New Reflectance Oximeter With the HewlettPackard Oximeter", 122–126, *Biomedical Instrumentation And Technology*, (March/April, 1990).

In accordance with one aspect of the present invention, chassis 12 may be configured for insertion into an anatomical canal, for example the esophagus or rectum of an animal or human. It is notable that many such cavities comprise a mucus membrane wall, a rich arterial bed site. Moreover, by employing a mucus membrane or similar anatomical sight for interrogation, many of the problems associated with non-invasive sensing are eliminated or reduced. For example, light reflectance from the surface of the epidermis is substantially eliminated at a mucus membrane site. In addition, various effects of external light are eliminated, inasmuch as internal anatomical cavities are typically devoid of ambient light. In addition, internal body cavities are often free of hair, fur, fingernails, toenails, cartilage, scar tissue, and many other factors which influence the ability to efficiently pass light through an arterial bed.

Thus, in accordance with a further aspect of the invention, it may be possible to manipulate chassis 12 to thereby optimally position the optics with respect to the cavity wall. For example, chassis 12 may be rotated about its longitudinal axis until a robust, stable output is achieved. In addition, it may be desirable to incorporate a balloon, analogous to balloons employed in balloon angioplasty, into chassis 12. More particularly and with momentary reference to FIG. 2, a small balloon may be placed at any point along chassis 12, for example at one of respective points B1 or B2 on the opposite side of chassis 12 from the optical components. Upon inserting chassis 12 into the anatomical cavity, the balloons may be inflated slightly to thereby bias emitter 22 and detector 28 against the cavity wall.

In accordance with one aspect of an alternate embodiment of the present invention, chassis 12 may suitably be substantially flat or, alternatively, have a first cross-sectional dimension which is significantly greater than a second transverse cross-sectional dimension (e.g., an ellipsoid), such that chassis 12 is substantially self-aligning within a body cavity. In this regard, it may also be desirable to place a first emitter assembly and a first detector assembly on one side of the chassis, and a second emitter assembly and a second detector assembly on the opposing side of the distal end of the same chassis, such that light is emitted in opposite directions, i.e., against two opposing walls of the cavity. In accordance with such an embodiment, the output signals from the first and second detector assemblies may be monitored such that the system selects the most desirable signal for display based on, inter alia, signal-to-noise ratio, signal strength, signal stability, and the like.

The foregoing embodiment employing redundant optical circuitry may be particularly advantageous in situations where the anatomical canal may be partially obstructed. For example, in a veterinary application involving horses, often a portion of the rectal canal may be obstructed by fecal matter. When chassis 12 is inserted into the rectal canal, it may become lodged between a canal wall (mucus membrane) and the fecal matter. By monitoring the signal derived from the cavity wall and comparing it to the signal derived from the electronics proximate the fecal matter, it may be possible to utilize the signal from the optoelectronics proximate the cavity wall and disregard the signal from the optics proximate the fecal matter.

In accordance with a further embodiment wherein chassis 12 may be employed in the birth canal or womb of a human or animal (e.g., by inserting the device through the vagina), it may be particularly desirable to employ redundant electronics to sense one or both of the oxygen saturation level of the mother, as well as that of the baby in the birth canal. Additionally, chassis 12 may be employed in a human or animal inner ear.

In accordance with a further aspect of the invention, chassis 12 may assume any desired shape to permit optimal placement of the electronics proximate the internal cavity wall. For example chassis 12 may suitably be of any desired shape, for example, "banana" shaped; such a configuration would tend to bias the optoelectronics against the cavity wall, for example, by disposing the optoelectronics at point B3 or B4 of chassis 12 (see FIG. 2A). With continued reference to FIG. 2A, it may also be desirable to incorporate a suitable selectively controllable spring mechanism into chassis 12, such that the arc may be increased or decreased in situ, as desired, to achieve optimal placement of the optoelectronics with respect to the cavity wall.

In accordance with yet a further aspect of the present invention, the oximetry optoelectronics may be suitably incorporated into other medical apparatus, including an endotracheal tube, temperature probe, and the like. For those situations in which invasive treatment is required, i.e., the use of an endotracheal tube or a core body temperature probe, pulse oximetry data may be obtained in accordance with the present invention without the need to insert additional invasive apparatus into the patent.

In accordance with yet a further aspect of the invention, a suitable handle 13 or other manual or visual indicia (See FIG. 2A) may be incorporated into the proximal end of chassis 12. Handle 13 permits the physician to dynamically control the degree of axial insertion of the device as well as the rotational position of the device to ensure optimal placement of the optoelectronics. In this regard, handle 13 may be any desired distance from the optoelectronics. By monitoring the position of handle 13 with respect to opening 52 of the anatomical cavity, the precise position of the optoelectronics within the cavity may be unambiguously inferred.

In accordance with yet a further aspect of the invention, various biocompatible lubricants may be employed in conjunction with device 12 to facilitate insertion and removal of the device. Since these lubricants are generally optically transparent at wavelengths of interest and present a DC or steady state attenuation of light only, they generally do not interfere with accurate oxygen readings. Moreover, for those embodiments wherein a controllable spring mechanism is used to control the arc associated with chassis 12 (FIG. 2A), or in those embodiments in which a balloon is employed to position the optoelectronics, these features may also be employed to ensure that chassis 12 remains in place for extended periods of time.

In accordance with a further aspect of the invention, any convenient wavelength or pair of wavelengths may be employed in conjunction with emitter circuit 22. In accordance with a particularly preferred embodiment, first LED 24 suitably emits light in the range of 540 to 690 nanometers, and preferably in the range of 650 to 670 nanometers, and most preferably 660 plus or minus 5 nanometers. Second LED 26 suitably emits light in the range of 880 to 940 nanometers, and preferably in the range of 890 to 920 nanometers, and most preferably 905 plus or minus 10 nanometers.

In accordance with a further aspect of the present invention, as previously briefly mentioned above, chassis 12 of probe assembly 10 may be suitably provided with devices or other implements useful in biasing and thereby maintaining emitter 22 and detector 28 against the cavity wall. In particular, the present inventors have found that optimal oximetric readings can be best obtained by coupling the sensor with the cavity tissue lining, thereby creating a desired optical path through the vascular bed of the tissue. Accordingly, chassis 12 can be suitably configured with a deployment device to bias emitter 22 and detector 28 against and/or into the tissue of an anatomical cavity. Preferred exemplary embodiments of the invention incorporating such deployment devices may utilize inflatable balloons, spring configurations and/or other mechanical assists. However, it should be appreciated that deployment devices useful in the context of the present invention are not limited to these exemplary embodiments.

Figure 4:
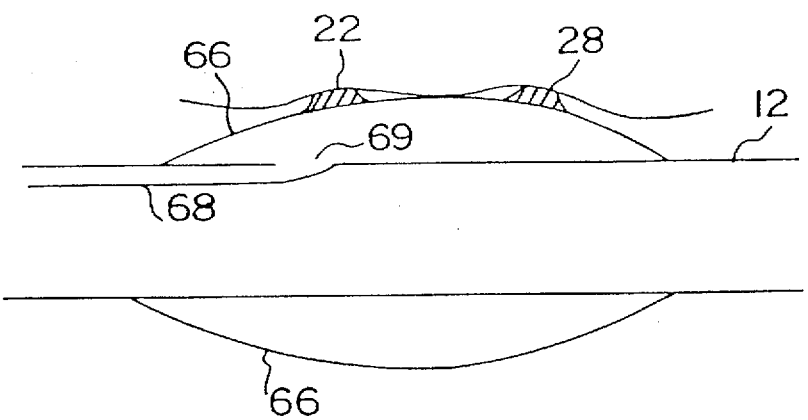
FIG. 4 shows a cross-sectional view of a portion of a further embodiment of a probe in accordance with the present invention utilizing an inflatable balloon biasing device.

Referring now to FIG. 4, a first exemplary embodiment of a deployment device useful in the context of the present invention comprises an inflatable balloon 66. In this illustrated embodiment inflatable balloon 66 is suitably attached to probe chassis 12. Emitter 22 and detector 28 are suitably firmly affixed to an outer surface of balloon 66. Preferably, emitter 22 and detector 28 are attached to balloon 66 in any conventional manner, such as through the use of adhesives or the like. For example, UV cure adhesives and the like may be employed. Balloon 66 is suitably attached to chassis 12 in any conventional manner. In accordance with one aspect of the present invention, balloon 66 is suitably molded to the exterior surface of chassis 12. Balloon 66 may comprise any conventional material, for example, latex. In the case where probe assembly 10 is used on humans as an esophageal probe, balloon 66 may advantageously comprise an endotracheal cuff (not shown) and be attached to chassis 12 in a conventional manner.

With continued reference to FIG. 4, balloon 66 is suitably inflated, such as by pumping air down the balloon inflation channel (tube) 68 into balloon 66. When balloon 66 is so inflated, emitter 22 and detector 28 are suitably pushed outward away from chassis 12 and biased against and into the anatomical cavity wall. Channel 68 communicates with balloon 66 through at least one port 69 extending through chassis 12. Air may then be pumped through channel 68 to balloon 66, using conventional monitors to control pressure, inflation rate, and/or the site of the inflated balloon. Axial and translational movement within the anatomical cavity is thus substantially inhibited for chassis 12 and, hence, the probe optics 10. Moreover, emitter 22 and detector 28 are suitably deployed into cavity wall 56 to thereby establish intimate contact therewith. It should be appreciated that while channel 68 is shown as extending along a wall of chassis 12, other orientations may be employed.

Figure 5:
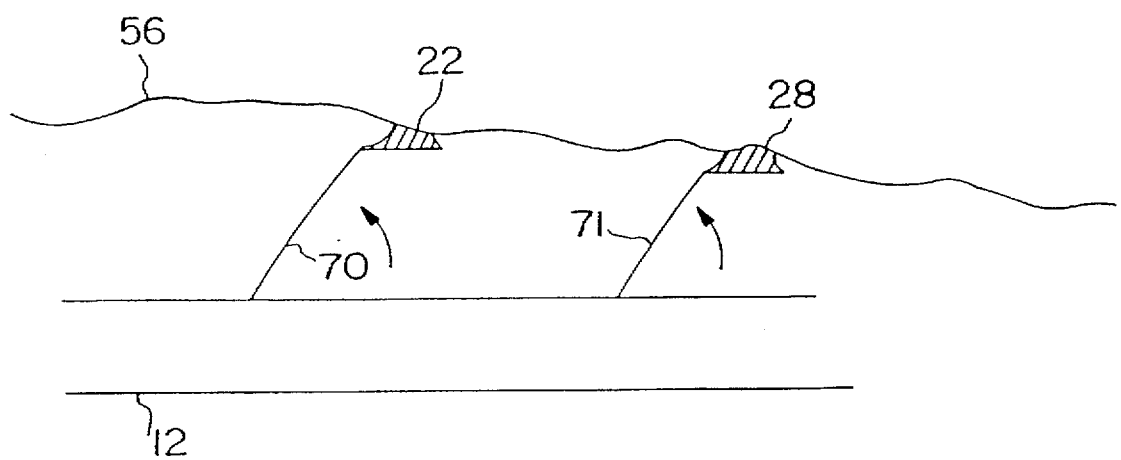
FIG. 5 shows a cross-sectional view of a portion of a further embodiment of a probe in accordance with the present invention within an anatomical canal utilizing an alternate biasing device.

In accordance with a further exemplary embodiment, a deployment device useful in connection with oximeter probe of the present invention may comprise a spring. With reference to FIG. 5, emitter 22 and detector 28 are advantageously attached to respective springs 70 and 71 such as through the use of any suitable adhesive or fastening mechanisms. Alternatively, the base of emitter 22 and detector 28 may be mechanically extruded onto or in conjunction with springs 70 and 71 during manufacture. As shown, springs 70 and 71 may be used to bias and deploy emitter 22 and detector 28 into anatomical cavity wall 56. In this illustrated embodiment, springs 70 and 71 suitably comprise leaf or other springs securely affixed to chassis 12 and also to emitter 22 and detector 28, respectively. Preferably, springs 70 and 71 are of a suitable size and dimension to advantageously bias emitter 22 and detector 28 into wall 56, and thus the particular size and dimension of springs 70 and 71 will depend upon the particular application. In the case where the probe assembly is used as an esophageal probe, springs 70 and 71 may be suitably configured to deploy emitter 22 and detector 28 from chassis 12 into the esophageal wall lining. Because the diameter of chassis 12 is typically much smaller than a fully distended esophagus, the springs are advantageously configured to accommodate radial extension in the range of 1 millimeter (mm) to 5 centimeters (cm), and most preferably about 3 cm.

While springs 70 and 71 are illustrated as leaf springs, it should be appreciated that coil or other similar springs which can be attached to chassis 12. Springs 70 and 71 may suitably comprise any flexible material, such as metal, plastic, rubber, thermoplastic and/or the like.

Figure 6:
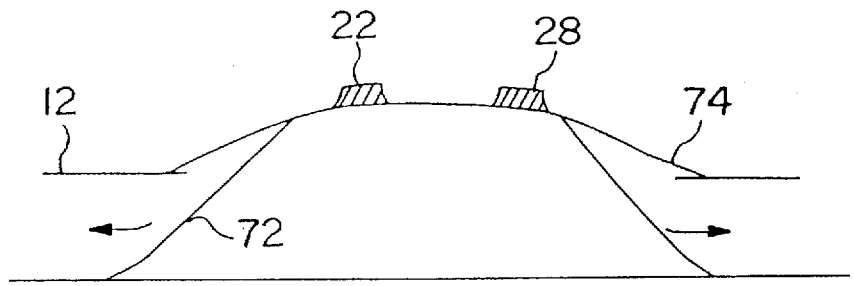
FIG. 6 shows a cross-sectional view of a portion of still a further embodiment of a probe in accordance with the present invention utilizing a further alternate biasing device.

In accordance with a further exemplary embodiment of the present invention, and with reference to FIG. 6, a deployment device useful in connection with oximeter probe assemblies of the present invention may suitably comprise a single retractable leaf spring 72 or the like. As shown in FIG. 6, spring 72 is preferably connected to a wall of chassis 12 and a flexible substrate 74 suitably affixed to an opposing wall of chassis 12. Substrate 74 may comprise a polymeric or metallic material, or any other material providing sufficient flexibility to deploy the optoelectronics into cavity wall 56. Emitter 22 and detector 28 are suitably attached to the outer surface of substrate 74 such that when spring 72 is actuated, it expands substrate 74 away from the outer surface of chassis 12 and biases emitter 22 and detector 28 against cavity wall 56. In connection with this aspect of the present invention, the probe assembly may be further provided with a device suitably configured to activate deployment device 72. For example, as the probe assembly is inserted into the anatomical cavity, it may be desirable to have spring 72 in a position where it does not engage substrate 74, and then, when probe 10 is suitably positioned within the cavity, cause device 72 to engage substrate 74 thus causing emitter 22 and detector 28 to be deployed. Any convenient mechanism may be used for this purpose, such as a push rod or the like.

Figure 10:
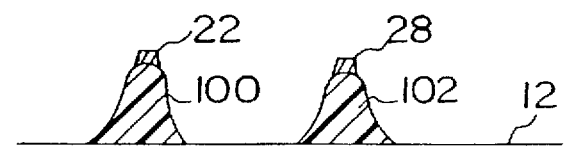
FIGS. 10 and 10A show cross-sectional views of a portion of further embodiments of probes in accordance with the present invention.
Figure 10A:
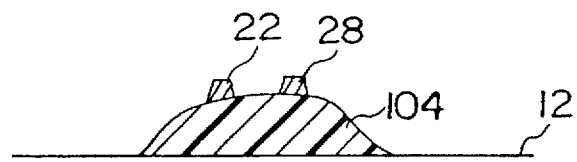

It should be appreciated that other deployment devices may be suitably used in connection with the present invention. For example, a single retractable leaf spring similar to spring 72 may be suitably attached to the external surface of chassis 12 and emitter 22 and detector 28 suitably attached thereto. Alternatively, in place of flexible springs or the like, the outer surface of tube 12 may simply be built up in the form of a single protuberance 104 (see FIG. 10A) or respective multiple protuberances 100 and 102 (see FIG. 10). In accordance with this aspect of the present invention, protuberances 100, 102 and 104 may be formed in any suitable fashion such as by molding silicon or other polymeric materials to the outer surface of chassis 12. As shown in FIGS. 10 and 10A, the electro-optical components associated with the probe assembly, namely emitter 22 and detector 28, may be advantageously affixed to such protuberances. While caution must be observed so that the overall dimension of probe assembly 10 in the region of the opto-electrical components is not excessively oversized, enlarging the dimension of chassis 12 to sufficiently deploy the electro-optical components into contact with cavity wall 56 should not have deleterious effects on cavity wall 56.

In general, in accordance with this aspect of the present invention, the electro-optical components utilized in connection with the subject probe are suitably attached to chassis 12 in a manner which enables them to be advantageously deployed into and/or against the wall of the anatomical cavity into which the probe is inserted. While various modifications may be made which are within the scope of the present invention, the illustrated embodiments shown herein offer low cost improvements over prior esophageal probes in that oximetry measurements can be efficiently and reliably obtained through use of a relatively low cost probe. Moreover, the deployment devices utilized in connection with the subject probe of the present invention, preferably offer the further advantage of minimizing movement of cavity 12 during interrogation.

Figure 7:
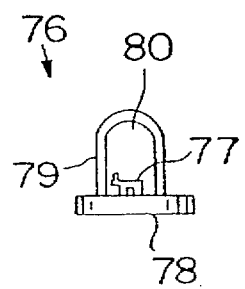
FIG. 7 is a side view of a sensor optical coupler useful in conjunction with a probe in accordance with the present invention.

In accordance with still a further aspect of the present invention shown in FIG. 7, a sensor optical coupler 76 may be advantageously configured to house the electro-optical components, namely emitter 22 and detector 28. Coupler 76 is suitably configured to permit effective optical communication between the electro-optical components, namely emitter 22 and detector 28, or similar electro-optical components.

Figure 7A:
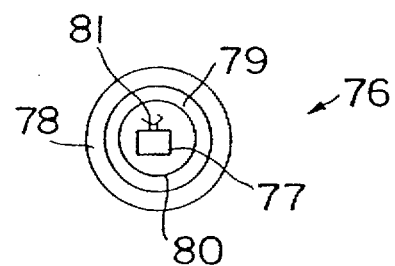
FIG. 7A is a top view of the coupler of FIG. 7.

With continued reference to FIG. 7A, coupler (button) 76 preferably comprises an electro-optical component 77 suitably affixed to a base (substrate) 78. A sleeve 79 is suitably attached to base 78 and configured to surround at least a portion of component 77. Sleeve 79 is suitably covered by a top 80 preferably exhibiting a substantially dome shaped profile. In accordance with a preferred aspect of this embodiment of the present invention, an optically opaque material, such as polymeric materials having optically opaque characteristics, e.g., black polyolethin and the like, may be utilized to form sleeve 79. On the other hand, top 80 preferably comprises any material having suitable optically transmissive properties to permit light to pass through top 80. Sleeve 79, top 80 and base 78 are suitably secured together by any convenient mechanism, such as UV cure optical grade adhesives, epoxies, acrylics, sorcones and/or the like.

Figure 7B:
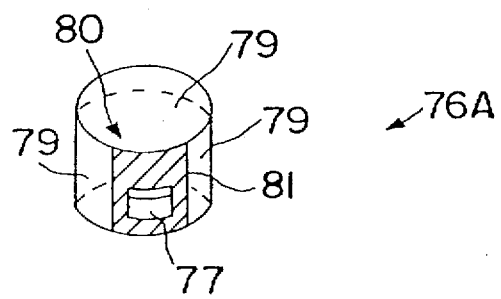
FIG. 7B is a perspective view of an alternate embodiment of a coupler useful in connection with a probe in accordance with the present invention.

Preferably, coupler 76 has a substantially cylindrical shape (see FIG. 7B) which provides a suitable housing for electro-optical component 77. In this regard, it should be appreciated that component 77 may comprise either LEDs 24, 26 (FIG. 1) used in emitter 22, or photodiode 30 (FIG. 1) used in detector 28.

Sleeve 79 and lens 80 cooperate to generally displace the anatomical fluids within the cavity in the region of component 77, thereby providing more direct contact between component 77 and the cavity wall, e.g., wall 56. Preferably, sleeve 79 and lens 80 cooperate to provide an optical contact region 81. For example, with reference to FIG. 7A, region 81 may advantageously comprise top 80 positioned at the top of sleeve 79. Alternatively, and with reference to FIG. 7B, region 81 may be formed in a side wall of the substantially cylindrical button 76A as a portion of sleeve 79.

In accordance with an aspect of this embodiment of the present invention, button 76 can be formed into substrate 78, or preferably directly onto a portion of probe chassis 12 or any deployment device used in connection therewith. Through use of such a probe assembly, reliable oximetric measurements can be obtained because, inter alia, the measurement site is near core body organs. Because of the close location of these organs and the lack of pigmentation in anatomical cavity walls, the oximetry signal may detect additional signals from other vascular sources, and thus potentially require that additional interpretation methods be employed to arrive at the appropriate determination of cavity tissue arterial oxygen saturation. While proper placement of the electro-optical components tends to avoid these difficulties, in accordance with a further embodiment of the present invention, electro-optical components are suitably positioned such that the optical path traverses only the cavity tissue and other vascular signals are substantially avoided.

Figure 8:
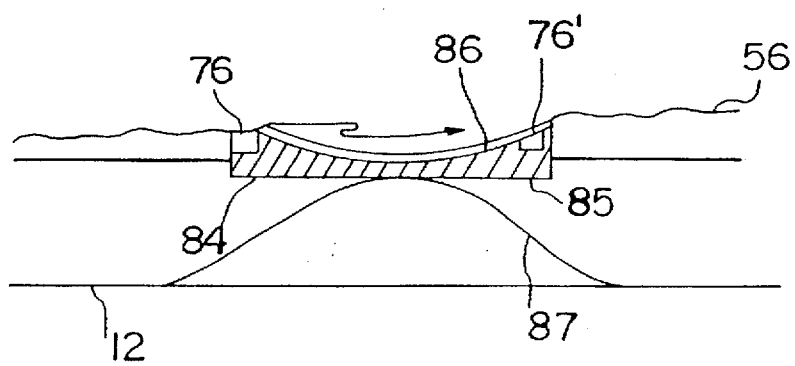
FIG. 8 shows cross-sectional view of a potion of yet another embodiment of a probe within an anatomical canal in accordance with the present invention utilizing an alternate sensor.

For example, and with reference now to FIG. 8, respective optical couplers 76, 76' can be affixed to a mounting platform 84. In accordance with this embodiment, optical coupler 76 suitably comprises respective LEDs similar to LEDs 24 and 26 (FIG. 1) as used in emitter 22; optical coupler 76' suitably comprises a photodiode similar to photodiode 30 (FIG. 1) as used in detector 28. In this illustrated embodiment, surface 84 preferably comprises a first surface 85 and a second surface 86. Preferably, couplers 76 and 76A are suitably mounted in surface 86 which, as shown, is optimally configured to exhibit a concave profile. Preferably, a deployment member 87 is suitably attached to surface 85 of platform 84. While any deployment device may be used, in the illustrated embodiment member 87 is suitably configured in a fashion similar to spring 72. In accordance with this embodiment, couplers 76 and 76' are provided with an optically transmissive top, such as shown in FIGS. 7 and 7A, and in operation are biased into cavity wall 56 such that wall 56 tends to conform to the configuration of platform 84. In this manner, the signal from coupler 76 to coupler 76' tends to follow a substantially straight optical path transversing substantially only the recessed tissue of wall 56. Thus, the probe advantageously can be used in this manner to obtain measurements of the cavity lining arterial oxygen saturation without receiving unwanted signals from other internal vascular sources. Depending on the geometry of platform 84, and a particularly of surface 86, a hybrid transmittance/reflectance optical system may be employed or, alternatively, a pure transmittance or pure reflectance system may be used.

Figure 9:
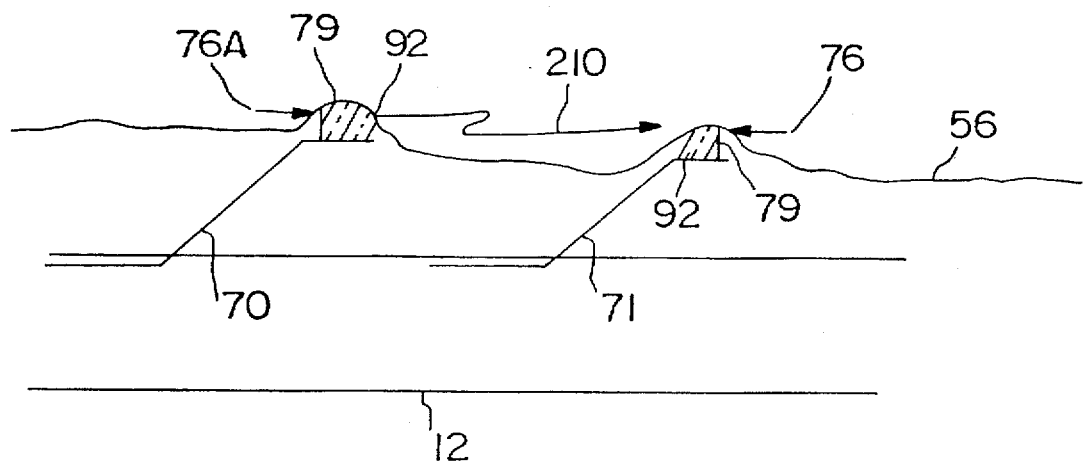
FIG. 9 shows a cross-sectional view of an alternate configuration of a probe in accordance with the present invention within an anatomical canal utilizing a further alternate sensor configuration employing the optical couplers of FIG. 7.

Referring now to FIG. 9, sensor optical couplers 76 and 76A (see FIG. 7B) can be used in connection with, for example, respective deployment devices 70 and 71 as shown in connection with FIG. 5. In accordance with this embodiment, sensor optical coupler 76A suitably comprises an emitter similar to emitter 22 and coupler 76 suitably comprises a detector similar to detector 28. As previously noted, optical couplers 76, 76A preferably comprise an optically opaque casing 79 that surrounds the sensor (either an emitter or a detector) which casing defines an optical contact region 81, generally in the form of an optically clear window denominated 92 in FIG. 9. As shown, windows 92 are suitably arranged such that window 92 of coupler 76A is facing window 92 of optical coupler 76, thus tending to establish a substantially straight optical path 210 between couplers 76 and 76A. In accordance with this embodiment, preferably couplers 76, 76A are affixed to one of the deployment devices discussed previously (e.g. springs), such that couplers 76, 76A are forced into contact with cavity wall 56 sufficiently deep enough that sufficient tissue overlies couplers 76 and 76A. As will be appreciated, the height of casing 79 can be adjusted as appropriate to allow for different configurations of window 92. For example, it may be desirable to configure the detector housing with a wider window than that which is provided in the emitter housing. For example, coupler 76 may have an optically opaque top and optically clear sides, or a window formed in the side which is wider than the corresponding window in coupler 76A.

In accordance with a further aspect of the present invention, coupler 76 can be suitably formed from an injection molded plastic or other polymeric material in any configuration which permits effective optical coupling between the electro-optical components of the probe assembly.

In accordance with yet a further aspect of the present invention, the probe assembly may be suitably configured to ensure that the probe is effectively stabilized within a body cavity. As generally discussed above in connection with FIGS. 4 to 10, by enlarging the diameter of the chassis or otherwise deploying the oximetry opto-electronics of the probe into engagement with a wall of the anatomical canal into which the probe is inserted, a certain degree of stabilization may be obtained. Nevertheless, in some applications, even greater control of the probe with respect to the anatomical canal may be desired. Further, by suitably configuring the probe, it is possible to more advantageously deploy oximeter sensors into surrounding tissue allowing for optimum optical coupling for reflective and transmissive oximetry sensing. Such a probe may be configured for use with humans as well as with other animals, birds and the like and may be used in any anatomical canal, such as the esophageal canal, rectal canal, or vaginal canal.

In accordance with this aspect of the present invention, the probe is preferably configured such that the oximetry opto-electronics are positioned and maintained in a generally blood perfuse region of a body cavity in which the probe is used. For example, the present inventors have found that locking the probe in a muscular region of a body canal enables the measurement of oximetry parameters (e.g. $SPO_2$) which is relatively unaffected by movements. In accordance with a preferred aspect, the muscle targeted comprises a sphincter-type muscle, such as, for example, the sphincter muscle in the rectal canal, the crico-pharyngeal (CP) muscle in the esophagus, and/or the like. As will be appreciated, such sphincter-type muscles function, such as when food or other objects approach the muscle, to contract and dilate thereby allowing the objects to pass. After the objects pass, the muscle again relaxes and constricts. Thus, in accordance with the various aspects of this embodiment of the invention, the probe is suitably configured to take advantage of the dilation and constriction of such muscle, e.g. the CP or other similar muscle, to secure and stabilize the probe within the anatomical canal, thus tending to inhibit movement of the probe while obtaining reliable oximetry readings. Such a configuration also serves to act as an esophageal diropter, preventing fluids and other matter from passing up and being aspirated by a patient.

One embodiment of such a probe may be configured for use within the esophageal canal of a human. With momentary reference to FIG. 13, When in place, the configuration of the probe enables stabilization of the probe in the crico-pharyngeal ("CP") muscle region 192 which borders the hypo-pharynx 194 and esophageal opening 190, approximately 13 cm to 15 cm from the back incisors of a typical adult. The CP muscle region has been found to be advantageous for pulse oximetry sensing because it is a generally uniform blood perfuse vascular region. It should be appreciated that while an aspect of this embodiment of the present invention will be described with reference to a probe assembly useful for oximetry sensing in the CP muscle region, the probe of this embodiment can be placed at any point within the esophageal canal or other anatomical canal that has a similar blood perfuse vascular presence.

Referring now to FIGS. 11A and 11B, in accordance with a preferred exemplary aspect of this embodiment of the present invention, a probe 110 suitably comprises a chassis 112 having a distal end 114, a proximal end 116, a deployment device 118, an emitter assembly 126 and a detector assembly 128. Probe 110 also preferably includes a plug assembly 132 which is suitably configured, as described hereinabove, for interaction with a control box serving to interpret data received from the devices, e.g. oximetry sensing devices, carried by probe 110. In addition, probe 110 may also comprise a handle 130 which, as will be described in greater detail below, may be useful in inserting probe 110 into an anatomical canal.

Emitter assembly 126 and detector assembly 128 may suitably comprise any embodiment of the emitter and detector assemblies previously described herein. Moreover, emitter assembly 126 and detector assembly 128 may be placed at any location on deployment device 118 which will yield optimal reflective or transmissive oximetry readings. The placement and orientation of emitter assembly 126 and detector assembly 128 may differ based on the anatomical canal in which probe 110 is placed, the vascularly perfuse region being monitored, and/or the type of animal involved.

In accordance with this aspect of this embodiment of the present invention, deployment device 118 preferably comprises an integrally formed stabilizing member on which emitter assembly 126 and detector assembly 128 are carried, and as a result of the configuration of device 118, suitably and stably deployed within the body canal. In such case, deployment device 118 may be made of any bio-compatible material suitable for use within a body cavity. In accordance with a preferred embodiment of the present invention, deployment device 118 may be constructed of soft polyvinyl chloride (PVC) having a derometer in the range of about 15 to about 60, more preferably in the range of about 25 to about 35, and optimally about 30. Moreover, because emitter assembly 126 and detector assembly 128 are light sensitive devices, it is suitably advantageous for the material used to make deployment device 118 to be a dark color. The darker colored material will prevent the light from emitter 126 from refracting around inside deployment device 118, causing inaccurate oximetry readings.

As will be discussed in greater detail below, probe 110 including device 118 may be suitably configured for oximetry sensing and/or sensing or control of other parameters. For example, and as will also be described in greater detail below, in accordance with one aspect of this embodiment of the present invention, deployment device 118 may be configured for retrofitting other devices, for example, esophageal stethoscopes or other anatomical cavity probes and/or like devices currently known or hereafter devised.

Figure 12A:
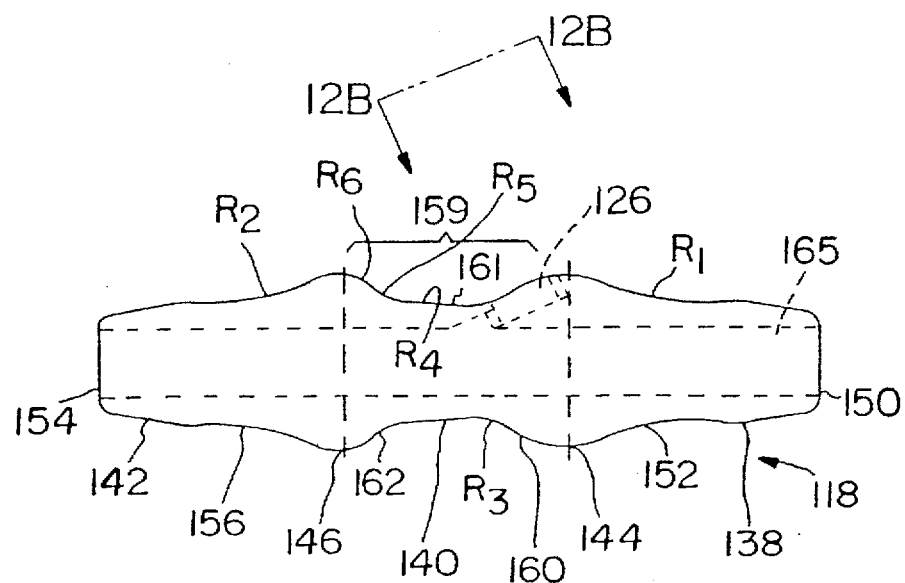
FIG. 12A is a side view showing a preferred configuration of a deployment device useful in connection with a probe in accordance with the present invention.
Figure 12B:
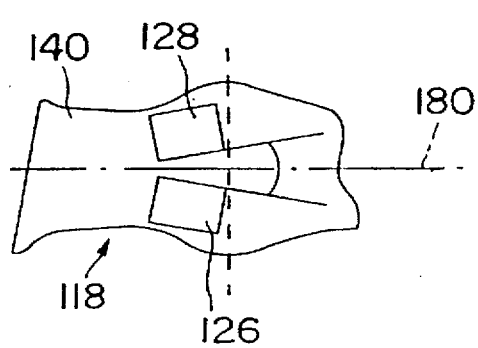
FIG. 12B shows a top view of a portion of the deployment device of FIG. 12A taken along the lines 12B—12B of FIG. 12A.
Figure 12C:
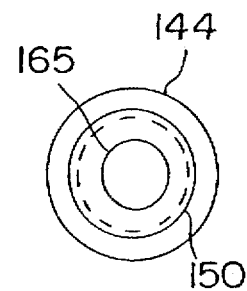
FIG. 12C is an end view of the deployment device of FIG. 12A.

Referring now to FIGS. 12A and 12C, and in accordance with a preferred aspect of this embodiment of the present invention, deployment device 118 may be a conformal-shaped tube having two enlarged lobes 144 and 146. Preferably, device 118 includes in seriatim, a first segment 138, first lobe 144, a second segment 140, second lobe 146 and a third segment 142. First segment 138 suitably includes a leading edge 150 and a substantially smooth sloped outer surface 152 evidencing a radius $R_1$ which terminates in lobe 144. Similarly, third segment 142 suitably includes a trailing edge 154 and a substantially smooth outer sloped surface 156 evidencing a radius $R_2$ which terminates in lobe 146. Second segment 140 suitably interconnects lobes 144 and 146 and preferably extends from the crest of lobe 144 to the crest of lobe 146. Segment 140 preferably evidences a substantially smooth sloped outer surface 159 which is preferably defined by a plurality of radii. In accordance with a particularly preferred aspect of this embodiment of the present invention, surface 159 is defined by respective radii $R_3$, $R_4$, $R_5$ and $R_6$ which cooperate to form an inner constricted region 161 bounded by respective outwardly extending sloped regions 160 and 162. As shown in FIG. 12A, device 118 so configured preferably evidences a generally circumferentially symmetrical hour-glass configuration. However, preferably, leading lobe 144 and trailing lobe 146 have different configurations to advantageously secure device 118 within the desired anatomical canal.

Figure 13:
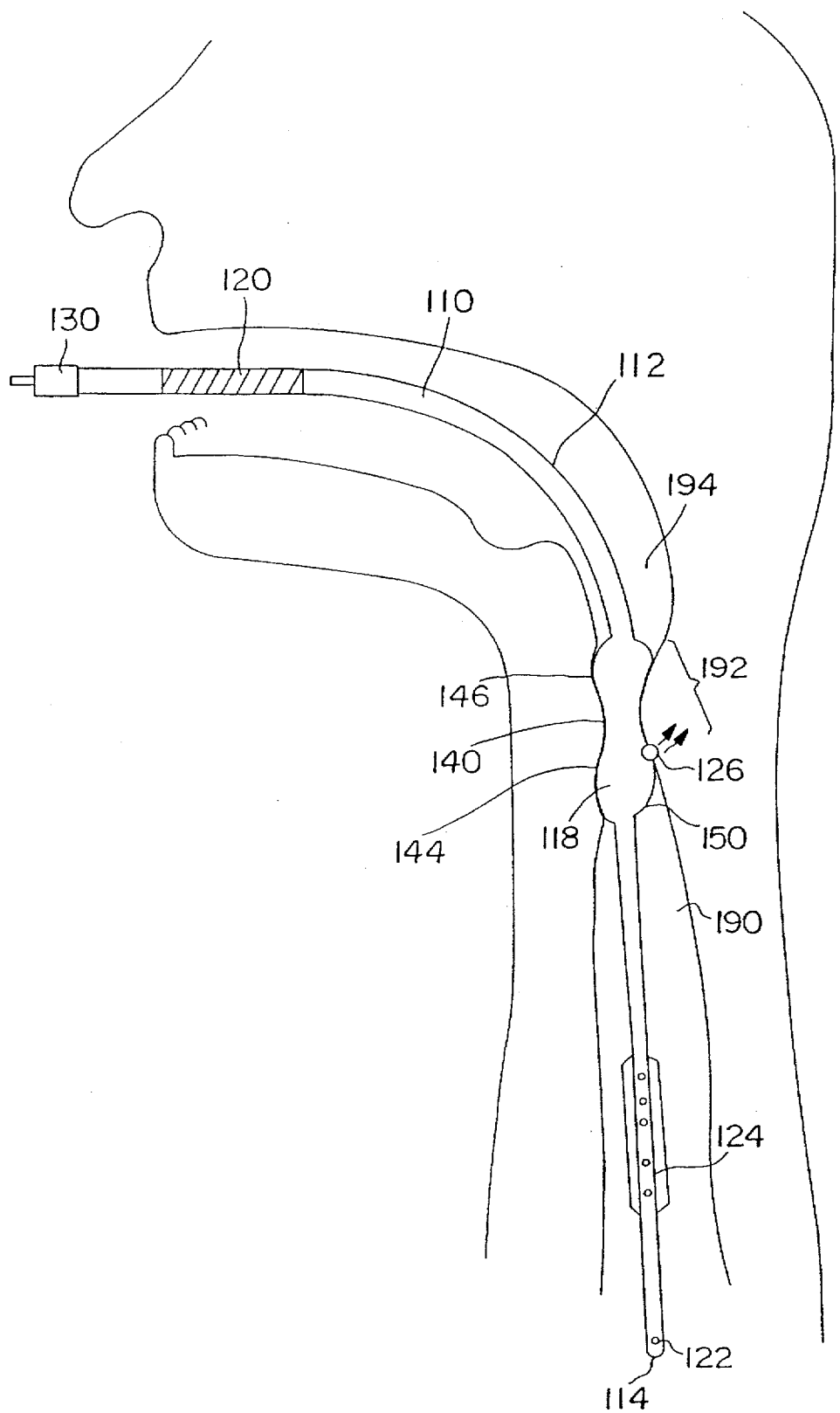
FIG. 13 shows a schematic representation of the probe of FIG. 11A within an anatomical canal (e.g. the esophagus)

To aid in the description of this aspect of the present invention, and with continued reference to FIG. 12A and momentary reference to FIG. 13, the use of device 118 will now be briefly described. When deployment device 118 is inserted into an anatomical canal, e.g. the esophagus, leading edge 150 enters into a muscle region, e.g. the CP muscle region, thereby causing the CP muscle to contract and dilate. This dilation advantageously allows first segment 138 of deployment device 118 to enter the CP muscle region. Continued insertion of the probe, and thus device 118 into the canal, e.g. the esophagus, causes lobe 144 to contract and interact with the CP muscle; through appropriate dimensioning of lobe 144, such interaction causes the CP muscle to relax and constrict. This constriction together with further insertion of the probe tends to cause the CP muscle to constrict further and substantially surround joining section 140 about region 161. Further insertion of probe 110 thus tends to be inhibited, in large part due to the appropriate dimensioning of lobe 146 and of segment 140. With further movement inhibited, emitter 126 and detector 128, preferably carried on an external portion of surface 159, are suitably deployed into a major portion of the CP muscle. Lobes 144 and 146 thus prevent deployment device 118 from migrating up or down the esophagus once probe 110 is in place thereby allowing substantially stable core oximetry measurements.

More particularly, and in accordance with a particularly preferred aspect of this embodiment of the present invention, lobes 144 and 146 and segments 138, 140 and 142 are suitably configured to encourage this stabilization and securing of device 118 into the CP muscle region. In general, segment 138 and lobe 144 are suitably dimensioned to occasion first contraction (Le. dilation) of the CP muscle, and thereafter as lobe 144 passes into the CP muscle region, relaxation (Le. contraction) of the CP muscle. Segment 140 and lobe 146, on the other hand, are, in general, preferably dimensioned to prevent further insertion of probe 110 and more preferably once such insertion is halted, to stabilize and prevent further natural movement of device 118 as may be occasioned by, for example, peristaltic movements within the CP muscle region. The result is the stabilization of device 118 in an oximetry-friendly region of the esophagus.

The various radii that define the various surfaces, particularly surfaces 152, 156, 160, 161 and 162, are also suitably selected to aid in and enhance such operation. Preferably, radius $R_1$ is selected to encourage dilation of the muscle, and thus preferably is in the range of about 2.0 to about 3.0 cm, optimally about 2.54 cm. Similarly, radius $R_2$ preferably is in the range of about 2.0 to about 3.0 cm, optimally about 2.54 cm.

Preferably, radius $R_3$ is selected to encourage contraction of the muscle, and thus preferably is in the range of about 0.04 to about 1.4 cm, and more preferably in the range of about 0.85 to about 1.1 cm, and optimally about 0.953 cm. Preferably, radii $R_4$, $R_5$ and $R_6$ are selected to prevent further movement, either by insertion of probe 110 or by natural peristaltic movements of the muscle, of device 118 once suitably positioned. Accordingly, preferably radius $R_4$ is suitably in the range of about 0.75 to about 1.5 cm, and more preferably in the range of about 0.9 to about 1.1 cm, and optimally about 1.01 cm. Preferably, radius $R_5$ is suitably in the range of about 0.25 to about 0.75 cm, more preferably in the range of about 0.4 to about 0.6 cm, and optimally about 0.477 cm. Finally, radius $R_6$ is generally in the range of about 0.4 to about 1.2 cm, and more preferably in the range of about 0.7 to about 0.9 cm, and optimally about 0.8 cm.

The other dimensions and configurations of the various surfaces of device 118 also are preferably optimized to aid in utilization of probe 110, including device 118. Thus, in accordance with a preferred aspect of this embodiment of the present invention, deployment device 118 preferably evidences a length in the range of about 2 to about 10 cm, more preferably in the range of about 5 to about 8 cm, and optimally about 6.99 cm. First segment 138 preferably evidences a length from leading edge 150 to the crest of lobe 144 which is in the range of about 1 to about 4 cm, more preferably in the range of about 2 to about 3 cm, and optimally about 2.54 cm. Similarly, third segment 142 preferably evidences a length from trailing edge 154 to the crest of lobe 146 which is generally in the range of about 1 to about 4 cm, and more preferably in the range of about 2 to about 3 cm, and optimally about 2.29 cm. Segment 140 preferably evidences a length from the crest of lobe 144 to the crest of lobe 146 which is generally in the range of about 0.25 to about 0.75 cm and more preferably in the range of about 0.35 to about 0.53 cm, and optimally about 0.445 cm.

In accordance with a preferred aspect of this embodiment of the Present invention, lobes 144 and 146 are also suitably configured to enhance use. Accordingly, the lobes 144 and 146 preferably evidence (at their respective crests) a diameter in the range of about 0.5 to about 2.5 cm, more preferably in the range of about 1.2 to about 2 cm and optimally about 1.6 cm. It should be understood that, lobes 144 and 146 may have different diameters. For example, in accordance with a further aspect of the present invention, it may be beneficial for lobe 146 to evidence a diameter greater than the diameter of lobe 144.

To aid with insertion, leading edge 150 preferable evidences a diameter which is advantageously smaller than the diameter of lobes 144 and 146. In accordance with a preferred aspect of this embodiment, leading edge 150 evidences a diameter which is in the range of about 0.2 to about 1.5 cm, more preferably in the range of about 0.8 to about 1 cm, and optimally about 0.89 cm. In addition, preferably the outermost portion of leading edge 148 is rounded so that it can pass through the esophageal canal with relative ease. While not necessarily important for effective use of device 118, preferably, trailing edge 154 is similarly dimensioned, and thus preferably is also rounded at its outermost portion and evidences a diameter on the order of about 0.2 to about 1.5 cm, optimally about 0.89 cm.

While the preferred dimensions and configuration of device 118 have now been described, it should be appreciated that device 118 suitably may evidence a wide variety of different configurations, providing such configurations also enable proper placement and securing of probe 110 in a suitable region of the anatomical canal in which probe 110 is inserted. For example, in accordance with one alternate aspect of the invention, segment 142 may be omitted. As discussed in greater detail below, for example in connection with the probe shown in FIG. 14, such a probe has been found to be particularly useful for insertion in rectal canals, particularly rectal canals of animals. Further alterations and modifications of the dimensions and configurations of the various segments and regions of device 118 may also be made, as will be appreciated or as may be hereafter devised by those skilled in the art in light of this disclosure.

With continued reference to FIGS. 12A and 12C, in accordance with a preferred aspect of this embodiment of the present invention, device 118 preferably evidences an axial lumen 165. Preferably, lumen 165 is substantially cylindrical and extends from leading edge 150 to trailing edge 154. Preferably, lumen 165 evidences a generally uniform diameter on the order of about 0.5 to about 0.75 cm, and optimally about 0.635 cm. Preferably, device 118 is mounted to chassis 112 such that chassis 112 extends through lumen 165. Alternatively, however, particularly in cases where probe 110 is configured primarily for oximetric sensing applications, lumen 165 may be suitably eliminated and chassis 112 merely attached to device 118, such as, for example, in proximity to trailing edge 154.

Referring now to FIG. 12B, in accordance with a preferred exemplary aspect of this embodiment of the present invention, emitter assembly 126 and detector assembly 128 are suitably mounted on device 118 such that optimum reflective oximetry measurements from a generally uniform vascular blood perfuse region, for example, the CP muscle region, may be obtained through use of probe 110. While the specific location of emitter 126 and detector 128 may be varied, as desired, preferably, such elements are suitably located on device 118 such that as device 118 is secured within a desired region, e.g. the CP muscle region, elements 126 and 128 are deployed into the anatomical canal wall for reflective or transmissive oximetry. In accordance with the illustrated embodiment, emitter 126 and detector 128 are suitably positioned such that reflective oximetry measurements may be obtained. In general, in accordance with this embodiment, emitter 126 and detector 128 are suitably positioned on surface 160 of segment 140 such that as device 118 is secured, elements 126 and ;128 are directed into the CP muscle which surrounds segment 140. Stated another way, as device 118, carried by probe 110, is inserted into the desired region, e.g. the CP muscle region, and the CP muscle constricts about device 118, elements 126 and 128 are advantageously positioned to be directed into the constricted muscle.

With reference to FIGS. 11A, 12A and 13, preferably, emitter 126 and detector 128 are mounted within segment 140 adjacent lobe 144, for example on surface 160. As previously generally noted, the downward slope of surface 160 is typically not as steep as the slope of surface 162. While depending on the size of detector assembly 128 and the size and intensity of emitter assembly 126, the spacial and angular orientation of emitter 126 and detector 128 with respect to each other may vary. In accordance with a preferred aspect of this embodiment of the present invention, emitter assembly 126 and detector assembly 128 are mounted in spaced relation on the order of about 0.5 to about 1.5 cm apart, and preferably in the range of about 0.8 to about 1.2 cm apart, and optimally about 1 cm apart. Further, and with particular reference to FIG. 12B, emitter assembly 126 and detector assembly 128 are preferably angled with respect to a center line 180 in the range of about 0° to about 45°, and more preferably in the range of about 5° to about 20°, and optimally about 10° away from center line 180. In this manner emitter 126 and detector 128 are optimally angled such that they are advantageously directed to the thickest portion of the CP muscle as it surrounds device 118.

While not illustrated in the drawing figures, emitter 126 and detector 128 may alternatively be positioned for transmissive oximetry. In such a configuration, for example, emitter 126 may advantageously be positioned on surface 160 of segment 140 and detector 128 on surface 162 of segment 140. As should be readily appreciated, when the opto-electronic assemblies are so positioned, oximetry measurements may be obtained as a result of the transmission of light from emitter 126 through the CP muscle surrounding device 118 and generally constricting about surface 161 and ultimately received by detector 128.

With reference to FIGS. 11A and 11 B, in accordance with a preferred aspect of this embodiment of the present invention, device 118 is suitably employed in connection with probe 110 such that effective and reliable core oximetry measurements are obtained when probe 110 is inserted into an anatomical canal. Although not shown in FIGS. 11A and 11 B, probe 110 may be suitably configured primarily for enabling oximetry measurements. In such case, probe 110 may terminate at or in proximity to leading edge 150 of device 118.

Alternatively, device 118 may be utilized in connection with a multi-parameter probe in connection with one aspect of this embodiment, device 118 is suitably installed, i.e. "retrofitted" onto a conventional device, such as an esophageal stethoscope and/or the like in a region suitable for appropriate alignment of elements 126 and 128 when such device is in use.

In accordance with a further aspect of this preferred embodiment of the present invention, probe 110 preferably may include, in addition to opto-electronic elements 126 and 128 disposed on device 118, a temperature measuring device 122, a pacing assembly 135, an acoustic monitor 124, and/or various combinations thereof. A preferred multi-parameter probe includes each of elements 122, 124, 135 as well as opto-electronic elements 126, 128. In accordance with this aspect Of the present invention, and as shown best in FIGS. 11A and 11B, a temperature measuring device 122 is suitably attached to probe 110 proximate distal end 114. Preferably, device 122 comprises a thermistor, preferably of conventional configuration and design. Preferably, in spaced relation between distal end 114 and device 118, acoustic monitor 124 may be formed. Preferably, monitor 124 comprises an acoustic diaphragm of conventional configuration and design.

In accordance with a further aspect of this embodiment of the present invention, pacing assembly 135 is suitably attached to probe 110 in a region intermediate of thermistor 122 and diaphragm 124. As best shown in FIGS. 11A and 11B, assembly 135 preferably comprises respective atrial pacing/recording electrodes 134a and 134b and respective ventricular pacing/recording electrodes 136a and 136b. Electrodes 134a and 134b are separated by a distance in the range of about 10 to about 30 cm, and more preferably in the range of about 18 to about 22 cm, and optimally about 20 cm. Electrodes 136a and 136b are similarly separated. Because the heart typically is angled in the chest cavity, ventricular electrodes 136a and 136b may be suitably rotated with respect to atrial electrodes 134a and 134b. For example, ventricular electrodes 136a and 136b may be rotated clockwise from atrial electrodes 134a and 134b in the range of about 0° to about 90°, more preferably in the range of about 30° to about 60°, and optimally about 45°.

In accordance with a preferred aspect of this further embodiment of the present invention, chassis 112 is of sufficient length to place segment 140 of device 118 within the CP muscle region as well as position temperature measuring device 122 and acoustic diaphragm 124 at optimal positions within the esophageal or other anatomical cavity. Chassis 112 evidences a length in the range of about 25 to about 75 cm, and preferably in the range of about 45 to about 65 cm, and most preferably in the range of about 52 to about 54 cm. To correctly position deployment device 118 at the CP muscle region, the center of segment 140 of device 118 is suitably positioned at a distance from proximal end 116 in the range of about 15 to about 35 cm, preferably about 25 to about 30 cm, and most preferably about 26 to about 28 cm. Acoustic diaphragm 124 is suitably located on chassis 112 of probe 110 such that the center of diaphragm 124 is located at a distance from proximal end 116 of about 30 to about 50 cm, more preferably from about 35 to about 45 cm, and most preferably about 39 to about 41 cm. A center point between electrodes 134a and 134b and proximal end 116 preferably is in the range of about 35 to about 55 cm, more preferably in the range of about 40 to about 45 cm, and optimally about 43 cm. Similarly, a center point between electrodes 136a and 136b and the center point between electrodes 134a and 134b is in the range of about 3 to about 10 cm, more preferably in the range of about 4 to about 6 cm, and optimally about 5 cm.

It should be noted that these lengths are disclosed herein as exemplary measurements suitable for use of a probe in accordance with the present invention configured for insertion into a human esophagus, and that the invention is not limited to these dimensions. The anatomical structure of other animals or other anatomical canals will cause the dimensions to vary accordingly.

To aid in proper insertion of probe 110, chassis 112 may include indicia useful for visually determining when probe 110 has been fully and properly inserted into an anatomical canal. Thus, in accordance with a further aspect of the present invention, probe 110 comprises a depth marker 120 which can serve as an indicator as to when probe 110 is inserted a proper distance. Depth marker 120 suitably may be placed on chassis 112 such that when it is at the mouth area, deployment device 118 is near the CP muscle region, and acoustic diaphragm 124 and temperature measuring device 122 are in their appropriate locations. Depth marker 120 may comprise indicia, such as markings, surface impressions, etc., formed on chassis 112. Preferably, depth marker 120 is positioned on chassis 112 a predetermined distance from proximal end 116 in the range of about 7 to about 20 cm, preferably about 10 to about 17 cm, and most preferably about 12 to about 14 cm.

Probe 110 may also be provided with handle 130 to aid in insertion of probe 110 into an anatomical canal. As shown best in FIG. 11 B, handle 130 suitably may be attached to proximal end 116 of probe 110.

Having now described the various aspects of probe 110, a preferred manner of inserting probe 110 will now be described with reference to FIG. 13. In accordance with this preferred embodiment of the present invention, a person (e.g. doctor, technician, etc.) will insert probe 110 through the mouth and into an esophageal cavity 190 of a patient causing leading edge 114, temperature measuring device 122 and acoustic diaphragm 124, etc. to pass down esophagus 190 to and through a CP muscle region 192. As probe 110 is further inserted, deployment device 118 is directed toward CP muscle 192. Because deployment device 118 is larger than chassis 112, leading edge 150 of deployment device 118 will generally stretch the membrane that precedes (i.e. is above) muscle 192, thereby causing activation of the neurons in the muscle and thus relaxation (Le. dilation) of muscle 192. Continued insertion of probe 110 results in lobe 144 being passed through muscle 192, which in turn tends to cause muscle 192 to contract and generally surround segment 140 of device 118. While insertion of probe 110 may halt at that point, preferably probe 110 is further inserted such that lobe 146 is also passed through muscle 192. In accordance with this aspect of the present invention, to thus set deployment device 118 of probe 110 in place, the direction of probe 110 is thereafter reversed such that lobe 146 backs up through CP muscle 192. Such movement tends to cause CP muscle 192 to relax and constrict upon segment 140. This constriction of muscle 192 tends to "lock" device 118 in place thus tending to deploy emitter assembly 126 and detector assembly 128 by embedding them into CP muscle region 192. In addition, due to the orientation of the elements of probe 110, once device 118 is suitably positioned, acoustic diaphragm 124, thermistor 122 and pacing assembly 135 will also be suitably positioned further within esophagus 190. This approximate positioning may be evident by alignment of a depth marker 120 within the mouth of the patient.

As previously briefly mentioned, in accordance with various aspects of this embodiment of the present invention, a probe may include deployment devices having configurations and dimensions varying from those described above with respect to device 118. For example, deployment devices used in other body cavities such as the rectal or vaginal cavities may have varying configurations so as to conform to the particular muscle or tissue within that cavity. Furthermore, the type of animal involved may cause the configuration to vary.

In particular, in accordance with a further aspect of this embodiment of the present invention, a deployment device may be suitably configured for use in the rectal canal of a human, a dog, a cat, a horse, or any other animal. In such case, the probe may generally comprise a deployment device suitably mounted to a handle or other introducer. As such, the dimensions and shape of deployment device 210 may vary depending on the animal for which the device is used. That is, the general size and shape of the probe comprising the deployment device may vary, as necessary, to fit the varying anatomical configurations of different animals or humans.

Figure 14:
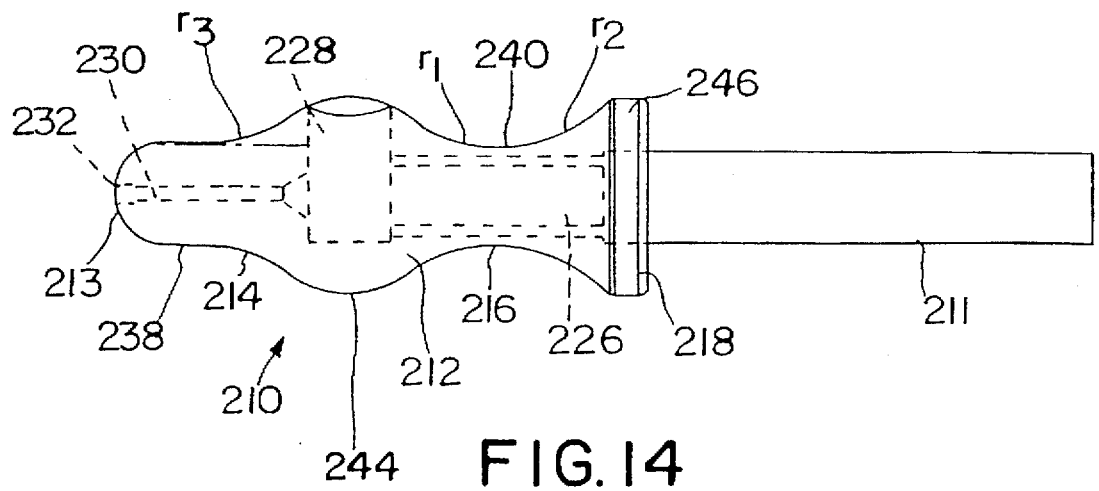
FIG. 14 shows an alternative configuration of a deployment device suitable for use in connection with a probe in accordance with the present invention.

Referring now to FIG. 14, in accordance with one aspect of the preferred embodiment, a probe 210 preferably comprises a rectal probe for dogs. As illustrated, probe 210 preferably includes a handle 211 secured to a body 212. As will be appreciated, body 212 bears a resemblance to deployment device 118, and as such generally comprises a first segment 238, a first lobe 244, second segment 240 and an enlarged region 246. First segment 238 preferably comprises a leading edge 213 and a generally sloped outer surface 214 which terminates at the crest of first lobe 244. Second segment 240, as shown, preferably evidences an enlarged diameter and communicates with trailing edge 218 of probe 210. Second segment 240 interconnects region 246 and lobe 244 and preferably includes a generally smooth rounded outer surface 216. In accordance with a preferred aspect of this embodiment of the present invention, surface 216 preferably is defined by various radii $r_1$, $r_2$. Radius $r_1$ preferably is in the range of about 0.2 to about 1.0 inch, more preferably in the range of about 0.3 to about 0.8 inch, and optimally about 0.61 inch. Preferably, radius $r_2$ evidences a larger radius and is typically on the order of between about 0.2 to about 2.5 inches, more preferably in the range of about 0.5 to about 1.5 inch, and optimally in the range of about 1.2 inch.

Surface 214 preferably also is defined by a radius $r_3$. Typically, radius $r_3$ is on the order of about 0.2 to about 1.0 inch, more preferably in the range of about 0.3 to about 0.8 inch, and optimally about 0.57 inch.

Preferably, leading edge 213 is also suitably rounded and is defined by a radius defined by its diameter. Preferably, leading edge 213 evidences a diameter in the range of about 0.2 to about 2.0 inches, more preferably in the range of about 0.4 to about 1.0 inch, and optimally about 0.55 inch.

As illustrated in FIG. 14, lobe 244 preferably evidences an enlarged diameter preferably on the order of about 0.2 to about 2.5 inches, more preferably about 0.5 to about 1.5 inch, and optimally about 1.1 inch. Similarly, enlarged region 246 preferably evidences an enlarged diameter which is on the order of about 0.2 to about 2.5 inches, more preferably in the range of about 0.5 to about 1.5 inch, and optimally about 1.0 inch.

Probe 210 preferably includes a first axial bore 226, a opto-electronic receiving cavity 228 and a second axial bore 230. Bore 226 is preferably threaded for, as will be discussed in greater detail below, receipt of handle 211. Cavity 228 preferably is configured centrally of lobe 244 and preferably communicates with at least one of the outer surfaces thereof. Bore 230 preferably communicates with leading edge 213 at a first end and with cavity 228 at a second end. The first end of bore 230 is suitably designed for receipt of, for example, a temperature measuring device (e.g. a thermistor (not shown)). Similarly, a void 232 is suitably designed to receive thermal-conductive material which allows heat to pass to the temperature measuring device. The thermal-conductive material allows the temperature measuring device to obtain more accurate temperature readings.

Figure 16:
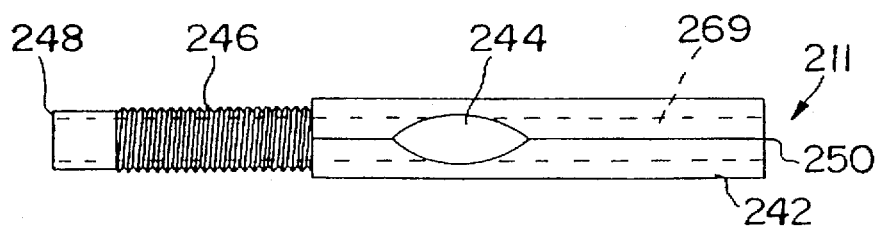
FIG. 16 is a side view of a handle suitable for use in connection with the deployment device of FIG. 14.

With reference to FIG. 16, handle 211 preferably comprises a grip section 242, a thumb indentation 244, a threaded section 246, a leading edge 248, and an alignment stripe 250. Threaded section 246 is suitably configured for receipt in threaded center bore 226, thereby securing handle 211 within probe 210. Handle 211 preferably includes an axial bore 269 suitably sized for passage of electrical wires and the like. Alignment stripe 250 aids a person (e.g. a doctor, technician or the like) in inserting the probe into the rectal canal at the correct angle, and is preferably aligned with the top center part of probe 210.

Figure 15:
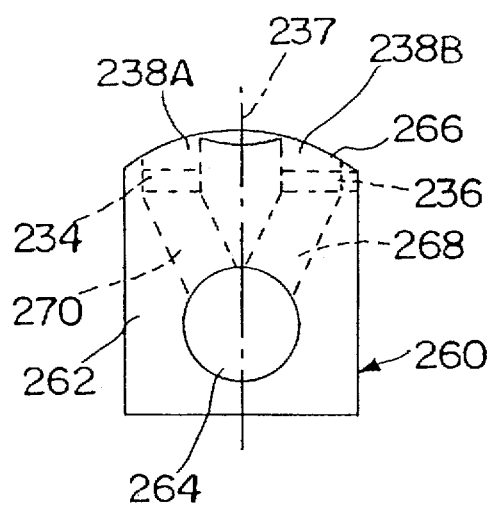
FIG. 15 shows a side view of a sensing assembly suitable for use in accordance with the deployment device shown in FIG. 14.

Cavity 228 is suitably dimensioned to receive an opto-electronic assembly 260. With reference to FIG. 15, assembly 260 preferably comprises a housing 262 including a central bore 264. As illustrated, housing 260 preferably comprises a generally cube-shaped base having a bottom and respective side walls which terminate in an arcuately shaped top 266. An emitter assembly 234 and a detector assembly 236 are suitably positioned adjacent top 266. Preferably, assemblies 234 and 236 are positioned such that the opto-electro components are directed toward top 266. Respective passageways 268 and 270 communicate with bore 264 and serve to permit passage of wiring from assemblies 234 and 236 to bore 264.

As discussed hereinabove with respect to probe 110, the spacial and angular orientation of assemblies 234 and 236 may vary based upon the type of animal, location of the probe, etc. In accordance with a preferred aspect of this embodiment of the invention and with continued reference to FIG. 15, emitter 234 and detector 236 are preferably positioned parallel to each other and parallel to a center line 237 of housing 260.

Housing 260 is preferably inserted into cavity 228 such that emitter 234 and detector 236 are suitably positioned near a surface of lobe 244. When housing 260 is so positioned, respective voids 238A and 238B may be evidenced due to the gap between the top of emitter 234 and detector 236 with reference to the outer surface of lobe 244. In order to ensure lobe 244 has a generally smooth surface, voids 238A and 238B preferably are filled with a transparent epoxy or the like to protect emitter 234 and detector 236 but allow the necessary light to pass therethrough.

In use, probe 210 is first assembled by inserting the various components. In accordance with a preferred aspect of this embodiment of the present invention, housing 260 containing opto-electro components 234 and 236 is preferably inserted into cavity 228. Necessary electrical wiring is provided. Such electrical wiring may be passed through various passageways contained within probe 210 and handle 211. Handle 211 is suitably attached to probe 210 by screwing threaded section 246 into thread receiving bore 226. If desired, additional elements such as a temperature measuring device (not shown) may be added, such as in receiving bore 230.

Once so assembled, probe 210 may be inserted into an anatomical canal, such as the rectal canal of an animal or human. In accordance with a preferred aspect of this embodiment of the present invention, probe 210 so configured is suitable for use in connection with dogs, horses, birds and the like. In accordance with such applications, probe 210 is first inserted into the rectal canal of such animal. In particular, leading edge 212 of probe 210 is first inserted into the opening of the rectal canal. Further insertion causes surface 214 to contact the sphincter muscle located in proximity to the opening of the rectal canal. Such contact causes the sphincter muscle to dilate and therefore permit passage of lobe 244 further into the rectal canal. As lobe 244 passes therethrough, the sphincter muscle tends to contract and surround surface 216 of segment 240 of probe 210. Further insertion of probe 210 is inhibited by enlarged region 246. With the sphincter muscle constricted about surface 216, opto-electro elements 234 and 236 are suitably deployed in the direction of the generally vascular blood profuse sphincter muscle. Reflectance oximetry measurements can thereby be obtained. In the event probe 210 is provided with a temperature measuring device, in addition, temperature measurements from the rectal canal can be reliably obtained.

It will be understood that the foregoing description is of preferred exemplary embodiments of the invention, and that the invention is .not limited to the specific forms shown. Various modifications may be made in the design and arrangement of the elements set forth herein without departing from the scope of the invention as expressed in the appended claims.

We claim:

1. A probe useful for invasively monitoring at best the oxygen saturation level of blood in at least one tissue wall of an esophagus, the probe comprising:

a chassis having a proximal end and a distal end;

an electrical connector extending from said proximal end of said chassis and terminating at a plug configured for connection to a pulse oximeter box;

an optics assembly configured to generate and transmit electrical signals to said oximeter box, said signals being indicative of the dynamic oxygen saturation level of blood in the wall tissue; and a deployment device attached to said chassis and configured to carry said optics assembly;

wherein said deployment device is configured to stabilize the probe in the esophagus and limit movement of the probe within the esophagus.

2. The probe of claim 1, wherein the deployment device is configured to reside in the crico-pharyngeal muscle region of the esophagus.

3. The probe of claim 1, further comprising a temperature measuring device connected to said chassis for measuring a temperature of a subject.

4. The probe of claim 1, further comprising a pacing assembly connected to said chassis for measuring heart pacing of a subject.

5. The probe of claim 1, further comprising an acoustic monitor connected to said chassis for monitoring sounds within the anatomical cavity of a subject.

6. A probe useful for invasively monitoring at least the oxygen saturation level of blood in a region of an anatomical cavity, the probe comprising:

a chassis having a proximal end and a distal end:

an electrical connector extending from said proximal end of said chassis and terminating at a plug configured for connection to a pulse oximeter box:

an optics assembly configured to generate and transmit electrical signals to said oximeter box, said signals being indicative of the dynamic oxygen saturation level of blood in a cavity wall tissue; and a deployment device attached to said chassis and configured to carry said optics assembly, said deployment device comprising:

means for causing a muscle in the region of the anatomical cavity to dilate allowing said deployment device to pass into the region including the muscle;

means for securing said deployment device in the muscle region when the muscle constricts, so that movement of the probe is inhibited; and means for biasing said optics assembly against tissue of the anatomical cavity.

7. The probe of claim 6 wherein said deployment device has a circumferentially symmetrical hour-glass configuration.

8. A probe useful for invasively monitoring at least the oxygen saturation level of blood in at least one tissue wall of a rectal canal, the probe comprising:

a chassis having a proximal end and a distal end;

an electrical connector extending from said proximal end of said chassis and terminating at a plug configured for connection to a pulse oximeter box:

an optics assembly configured to generate and transmit electrical signals to said oximeter box, said signals being indicative of the dynamic oxygen saturation level of blood in the wall tissue: and a deployment device attached to said chassis and configured to carry said optics assembly, and wherein said deployment device is configured to stabilize the probe in the rectal canal and limit movement of the probe within the rectal canal.

9. The probe of claim 8, wherein the deployment device is configured to reside in the sphincter muscle region of the rectal canal.

10. The probe of claim 8, wherein said deployment device comprises:

a first lobe having a crest and a substantially smooth outer surface;

a first segment having a leading edge and a generally sloped outer surface terminating at said crest of said first lobe; and a second segment having a trailing edge and a generally sloped outer surface terminating at the crest of said first lobe.

11. The probe of claim 10 wherein the leading edge of said first segment causes a muscle in the rectal canal to dilate allowing said deployment device to pass into a region including the muscle, and wherein the muscle then constricts around said second segment between said first lobe and said trailing edge such that movement of the probe is inhibited and said optics assembly carried by said deployment device is biased into a tissue of the rectal canal.

12. The probe of claim 10, wherein said deployment device is connected to a handle, said handle configured to aid in the insertion of said deployment device into the rectal canal.

13. The probe of claim 10, wherein the leading edge of said second segment further comprises a temperature measuring device.

14. The probe of claim 10, wherein said optics assembly is located near the outer surface of said first lobe and comprises an emitter assembly and a detector assembly, and wherein the emitter assembly is parallel to and in close proximity to the detector assembly, each said emitter assembly and detector assembly being directed perpendicular to a center axis of the deployment device toward the outer surface of said first lobe.

15. A probe useful for invasively monitoring at least the oxygen saturation level of blood in a region of an anatomical cavity, the probe comprising:

a chassis having a proximal end and a distal end;

an electrical connector extending from said proximal end of said chassis and terminating at a plug configured for connection to a pulse oximeter box;

an optics assembly configured to generate and transmit electrical signals to said oximeter box, said signals being indicative of the dynamic oxygen saturation level of blood in a cavity wall tissue; and a deployment device attached to said chassis and configured to carry said optics assembly, said deployment device comprising:

a first lobe and a second lobe, each lobe having a crest and a substantially smooth outer surface; and a first segment having a substantially smooth, hyperboloid shaped outer surface extending from the crest of said first lobe to the crest of said second lobe interconnecting said first lobe with said second lobe, wherein the outer surface of said first segment further comprises a first slope adjacent to said first lobe and a second slope adjacent to said second lobe.

16. The probe of claim 15 wherein said deployment device further comprises:

a second segment having a leading edge and a substantially smooth sloped outer surface terminating at said first lobe; and a third segment having a trailing edge and a substantially smooth sloped outer surface terminating at said second lobe.

17. The probe of claim 16, wherein the leading edge of said second segment is configured to cause a muscle in the region of the anatomical cavity to dilate allowing said deployment device to pass into the region including the muscle, and wherein said first segment is configured such that the muscle then constricts around said first segment between said first lobe and said second lobe such that movement of the probe is inhibited and said optics assembly carried by said deployment device is biased against a tissue of the anatomical cavity.

18. The probe of claim 17, wherein said optics assembly is configured for reflective oximetry measurements, said optics assembly comprising an emitter assembly and a detector assembly mounted in spaced relation near the surface of said first segment on the first slope adjacent to said first lobe, such that when the muscle constricts around said first segment, the emitter assembly and the detector assembly are biased against the muscle so that during operation, a signal from the emitter assembly passes into the muscle, reflects off and through the muscle tissue back into the detector assembly, thereby obtaining a reflective oximetry reading.

19. The probe of claim 17, wherein said optics assembly is configured for transmissive oximetry readings, the optics assembly comprising an emitter assembly and a detector assembly, the emitter assembly being mounted near the surface of said first segment on the first slope adjacent to said first lobe and the detector assembly is mounted near the surface of said first segment on the second slope adjacent to said second lobe, such that when the muscle constricts around said first segment, the emitter assembly and the detector assembly are biased against the muscle so that during operation, a signal from the emitter assembly passes through the muscle tissue to the detector assembly, thereby obtaining a transmissive oximetry reading.

20. The probe of claim 15, wherein said deployment device is made of a soft polyvinyl chloride having a durometer in the range of 15 to 60.

21. The probe of claim 15, wherein said deployment device comprises optically non-reflective and non-transmissive material.

22. A probe configured for insertion into an anatomical cavity for invasively monitoring bodily functions of a patient, the probe comprising:
a chassis having a proximal end and a distal end;
an electrical connector extending from the proximal end of said chassis and configured for connection to a monitoring device; and
a deployment device attached to said chassis and configured to carry an optics assembly, wherein said deployment device is configured to limit movement of the probe within the anatomical cavity and enable measurement by said optics assembly of a dynamic oxygen saturation level of blood in tissue of at least one tissue wall of the anatomical cavity, said optics assembly configured to generate and transmit electrical signals indicative of the dynamic oxygen saturation level of the blood in the tissue to the monitoring device.

23. The probe of claim 22, further comprising:
a temperature measuring device attached to the distal end of said chassis, wherein said temperature measuring device is configured to generate and transmit electrical signals to the monitoring device, the signals being indicative of a temperature of the patient;
an acoustic monitoring device positioned in spaced relation between said temperature measuring device and said deployment device, said acoustic monitoring device configured to receive sounds within the anatomical cavity and to generate and transmit electrical signals to the monitoring device, the signals being indicative of the received sounds; and
a pacing assembly positioned in spaced relation between said temperature measuring device and said acoustic monitoring device, said pacing assembly configured to monitor heart pacing of the patient and to generate and transmit electrical signals to the monitoring device, the signals being indicative of the heart pacing.

24. The probe of claim 23, wherein said pacing assembly comprises an atrial pacing/recording electrode and a ventricular pacing/recording electrode.

25. The probe of claim 24, wherein the atrial pacing/recording electrode is rotated clockwise on the chassis with respect to the ventricular pacing/recording electrode in the range of 30 degrees to 60 degrees.

26. A probe useful for invasively monitoring at least the oxygen saturation level of blood in a region of an anatomical cavity, the probe comprising:
a chassis having a proximal end and a distal end;
an electrical connector extending from the proximal end of the chassis and terminating at a plug configured for connection to a pulse oximeter box;
an optics assembly configured to generate and transmit electrical signals to the pulse oximeter box, the signals being indicative of a dynamic oxygen saturation level of blood in a cavity wall tissue;
a deployment device attached to the chassis, wherein the optics assembly is carried by the deployment device having a circumferentially symmetrical hour-glass configuration.

27. A method for invasively monitoring the oxygen saturation level of blood in a muscle region of an anatomical canal, comprising the steps of:
providing a probe having a chassis, an electrical connector and an optics assembly comprising an emitter and a detector, said optics assembly being carried on a deployment device having first, second and third segments and first and second lobes said optics assembly being carried on the second segment;
inserting a distal end of said probe into the canal;
guiding said probe into the muscle region of the canal until the first segment of the deployment device engages the muscle;
inserting the deployment device of said probe further into the muscle region until the second segment of the deployment device passes the muscle region such that the deployment device is substantially secured in the muscle region, and the optics assembly is biased against the muscle;
configuring an optical path between the emitter and the detector of the optics assembly, such that an oximetry signal passes through the blood perfused muscle from the emitter to the detector; and
evaluating the signals received by the detector to monitor the oxygen saturation level of the blood.

28. The method of claim 27 further comprising the steps of:
inserting the deployment device of the probe further into the muscle region until said third segment passes the muscle region;
reversing the direction of the probe such that the third segment backs up through the muscle region securing the deployment device in the muscle region, such that the optics assembly contained in the second segment of the deployment device is biased against the muscle tissue.

29. A multi-parameter probe configured for insertion into an anatomical cavity for invasively monitoring bodily functions of a patient, the probe comprising:

a chassis having a proximal end and a distal end;

an electrical connector extending from the proximal end of said chassis and configured for connection to a monitoring device;

an optics assembly configured to generate and transmit electrical signals to the monitoring device, the signals being indicative of a dynamic oxygen saturation level of blood in a cavity wall tissue;

a deployment device attached to said chassis and configured to carry said optics assembly, said deployment device having a circumferentially symmetrical hourglass configuration;

a temperature measuring device attached to the distal end of said chassis, wherein said temperature measuring device is configured to generate and transmit electrical signals to the monitoring device, the signals being indicative of a temperature of the patient;

an acoustic monitoring device positioned in spaced relation between said temperature measuring device and said deployment device, said acoustic monitoring device configured to receive sounds within the anatomical cavity and to generate and transmit electrical signals to the monitoring device, the signals being indicative of the received sounds; and a pacing assembly positioned in spaced relation between said temperature measuring device and said acoustic monitoring device, said pacing assembly configured to monitor heart pacing of the patient and to generate and transmit electrical signals to the monitoring device, the signals being indicative of the heart pacing.

30. A multi-parameter probe configured for insertion into an anatomical cavity for invasively monitoring bodily functions of a patient, the probe comprising:

a chassis having a proximal end and a distal end;

an electrical connector extending from the proximal end of said chassis and configured for connection to a monitoring device;

an optics assembly configured to generate and transmit electrical signals to the monitoring device, the signals being indicative of a dynamic oxygen saturation level of blood in a cavity wall tissue;

a deployment device attached to said chassis and configured to carry said optics assembly, said deployment device, comprising;
  a first lobe and a second lobe, each lobe having a crest and a substantially smooth outer surface; and
  a first segment having a substantially smooth, hyperboloid shaped outer surface extending from the crest of the first lobe to the crest of the second lobe interconnecting the first lobe with the second lobe, wherein the outer surface of said first segment further comprises a first slope adjacent to the first lobe and a second slope adjacent to the second lobe;

a temperature measuring device attached to the distal end of said chassis, wherein said temperature measuring device is configured to generate and transmit electrical signals to the monitoring device, the signals being indicative of a temperature of the patient;

an acoustic monitoring device positioned in spaced relation between said temperature measuring device and said deployment device, said acoustic monitoring device configured to receive sounds within the anatomical cavity and to generate and transmit electrical signals to the monitoring device, the signals being indicative of the received sounds; and a pacing assembly positioned in spaced relation between said temperature measuring device and said acoustic monitoring device, said pacing assembly configured to monitor heart pacing of the patient and to generate and transmit electrical signals to the monitoring device, the signals being indicative of the heart pacing.

31. The probe of claim 30 wherein said deployment device further comprises:

a second segment having a leading edge and a substantially smooth sloped outer surface terminating at the first lobe; and a third segment having a trailing edge and a substantially smooth sloped outer surface terminating at the second lobe.

32. The probe of claim 31, wherein the leading edge of said second segment is configured to cause a muscle in the region of the anatomical cavity to dilate allowing said deployment device to pass into the region including the muscle, and wherein said first segment is configured such that the muscle then constricts around said first segment between said first lobe and said second lobe such that movement of the probe is inhibited and said optics assembly carried by said deployment device is biased against a tissue of the anatomical cavity.

33. The probe of claim 32, wherein said optics assembly is configured for reflective oximetry measurements, said optics assembly comprising an emitter assembly and a detector assembly mounted in spaced relation near the surface of said first segment on the first slope adjacent to said first lobe, such that when the muscle constricts around said first segment, the emitter assembly and the detector assembly are biased against the muscle so that during operation, a signal from the emitter assembly passes into the muscle, reflects off and through the muscle tissue back into the detector assembly, thereby obtaining a reflective oximetry reading.

34. The probe of claim 32, wherein said optics assembly is configured for transmissive oximetry readings, said optics assembly comprising an emitter assembly and a detector assembly, the emitter assembly being mounted near the surface of said first segment on the first slope adjacent to said first lobe and the detector assembly is mounted near the surface of said first segment on the second slope adjacent to said second lobe, such that when the muscle constricts around said first segment, the emitter assembly and the detector assembly are biased against the muscle so that during operation, a signal from the emitter assembly passes through the muscle tissue to the detector assembly, thereby obtaining a transmissive oximetry reading.

* * * * *